(12) United States Patent
Keitz et al.

(10) Patent No.: US 11,897,915 B2
(45) Date of Patent: Feb. 13, 2024

(54) SUGAR DERIVATIVES AND USES THEREOF TO PREPARE NOVEL SENOLYTIC AGENTS

(71) Applicant: Rubedo Life Sciences, Inc., Sunnyvale, CA (US)

(72) Inventors: Paul Keitz, Redwood City, CA (US); Gus Bergnes, Pacifica, CA (US); Mark A. Gallop, San Francisco, CA (US); Marco Quarta, Oakland, CA (US)

(73) Assignee: Rubedo Life Sciences, Inc., Sunnyvale, CA (US)

( * ) Notice: Subject to any disclaimer, the term of this patent is extended or adjusted under 35 U.S.C. 154(b) by 0 days.

(21) Appl. No.: 17/944,019

(22) Filed: Sep. 13, 2022

(65) Prior Publication Data

US 2023/0096764 A1     Mar. 30, 2023

Related U.S. Application Data

(60) Provisional application No. 63/243,542, filed on Sep. 13, 2021.

(51) Int. Cl.
| | | |
|---|---|---|
| *C07H 9/04* | (2006.01) | |
| *C07H 15/26* | (2006.01) | |
| *C07H 23/00* | (2006.01) | |
| *C07H 7/02* | (2006.01) | |

(52) U.S. Cl.
CPC ............ *C07H 9/04* (2013.01); *C07H 7/02* (2013.01); *C07H 15/26* (2013.01); *C07H 23/00* (2013.01)

(58) Field of Classification Search
None
See application file for complete search history.

(56) References Cited

U.S. PATENT DOCUMENTS

| | | | |
|---|---|---|---|
| 6,706,888 B2 | 3/2004 | Chae et al. | |
| 11,026,963 B2 | 6/2021 | Gallop et al. | |
| 2016/0339019 A1 | 11/2016 | Laberge et al. | |
| 2020/0016185 A1* | 1/2020 | Gallop | C07H 5/04 |

OTHER PUBLICATIONS

Childs, B., Gluscevic, M., Baker, D. et al. Senescent cells: an emerging target for diseases of ageing. Nat Rev Drug Discov 16, 718-735 (2017). <https://doi.org/10.1038/nrd.2017.116>.
Demaria M, O'Leary MN, Chang J, Shao L, Liu S, Alimirah F, Koenig K, Le C, Mitin N, Deal AM, Alston S, Academia EC, Kilmarx S, Valdovinos A, Wang B, de Bruin A, Kennedy BK, Melov S, Zhou D, Sharpless NE, Muss H, Campisi J. Cellular Senescence Promotes Adverse Effects of Chemotherapy and Cancer Relapse. Cancer Discov. Feb. 2017;7(2):165-176. doi: 10.1158/2159-8290. CD-16-0241. Epub Dec. 15, 2016. PMID: 27979832; PMCID: PMC5296251.
Schafer, M., White, T., Iijima, K. et al. Cellular senescence mediates fibrotic pulmonary disease. Nat Commun 8, 14532 (2017). <https://doi.org/10.1038/ncomms14532>.
Zhu Y, Doomebal EJ, Pirtskhalava T, Giorgadze N, Wentworth M, Fuhrmann-Stroissnigg H, Niedernhofer LJ, Robbins PD, Tchkonia T, Kirkland JL. New agents that target senescent cells: the flavone, fisetin, and the BCL-XL inhibitors, A1331852 and A1155463. Aging (Albany NY). Mar. 8, 2017;9(3):955-963. doi: 10.18632/aging.101202. PMID: 28273655; PMCID: PMC5391241.
Yosef R, Pilpel N, Tokarsky-Amiel R, Biran A, Ovadya Y, Cohen S, Vadai E, Dassa L, Shahar E, Condiotti R, Ben-Porath I, Krizhanovsky V. Directed elimination of senescent cells by inhibition of BCL-W and BCL-XL. Nat Commun. Apr. 6, 2016;7:11190. doi: 10.1038/ncomms11190. PMID: 27048913; PMCID: PMC4823827.
Zhu Y, Ichkonia I, Pirtskhalava I, Gower AC, Ding H, Giorgadze N, Palmer AK, Ikeno Y, Hubbard GB, Lenburg M, O'Hara SP, LaRusso NF, Miller JD, Roos CM, Verzosa GC, LeBrasseur NK, Wren JD, Farr JN, Khosla S, Stout MB, McGowan SJ, Fuhrmann-Stroissnigg H, Gurkar AU, Zhao J, Colangelo D, Dorronsoro A, Ling YY, Barghouthy AS, Navarro DC, Sano T, Robbins PD, Niedernhofer LJ, Kirkland JL. The Achilles' heel of senescent cells: from transcriptome to senolytic drugs. Aging Cell. Aug. 2015;14(4):644-58. doi: 10.1111/acel.12344. Epub Apr. 22, 2015.
Whittaker SR, Mallinger A, Workman P, Clarke PA. Inhibitors of cyclin-dependent kinases as cancer therapeutics. Pharmacol Ther. May 2017;173:83-105. doi: 10.1016/j.pharmthera.2017.02.008. Epub Feb. 5, 2017. PMID: 28174091; PMCID: PMC6141011.
Laberge RM, Sun Y, Orjalo AV, Patil CK, Freund A, Zhou L, Curran SC, Davalos AR, Wilson-Edell KA, Liu S, Limbad C, Demaria M, Li P, Hubbard GB, Ikeno Y, Javors M, Desprez PY, Benz CC, Kapahi P, Nelson PS, Campisi J. MTOR regulates the pro-tumorigenic senescence-associated secretory phenotype by promoting IL1A translation. Nat Cell Biol. Aug. 2015;17(8):1049-61. doi: 10.1038/ncb3195. Epub Jul. 6, 2015. Erratum in: Nat Cell Biol. May 2021;23(5):564-565. PMID: 26147250; PMCID: PMC4691706.
Fuhrmann-Stroissnigg, H., Ling, Y.Y., Zhao, J. et al. Identification of HSP90 inhibitors as a novel class of senolytics. Nat Commun 8, 422 (2017). <https://doi.org/10.1038/s41467-017-00314-z>.
Samaraweera, L., Adomako, A., Rodriguez-Gabin, A. et al. A Novel Indication for Panobinostat as a Senolytic Drug in NSCLC and HNSCC. Sci Rep 7, 1900 (2017). <https://doi.org/10.1038/s41598-017-01964-1>.
Guillory, K., Chapter 5, pp. 202-205 in Polymorphism in Pharmaceutical Solids, (Brittain, H. ed.), Marcel Dekker, Inc., New York, NY, 1999).
Grindley, T. Bruce, and Rasiah Thangarasa. "Selective mono-esterification and alkylation of 1, 6-anhydro-ß-d-glucopyranose via its dibutylstannylene derivative." Carbohydrate research 172.2 (1988): 311-318.
U.S. Appl. No. 17/943,824, filed Sep. 13, 2022, First Named Inventor : Marco Quarta; 152 pages.
U.S. Appl. No. 17/943,836, filed Sep. 13, 2022, First Named Inventor : Paul Keitz; 86 pages.
Holodiag, Pharmaparc II, Voie de l'Innovation, 27 100 Val de Reuil, France; accessed Jun. 29, 2023 http://www.holodiag.com.

\* cited by examiner

*Primary Examiner* — Traviss C McIntosh, III
(74) *Attorney, Agent, or Firm* — Young Basile Hanlon & MacFarlane, P.C.

(57) ABSTRACT

Provided herein are novel sugar derivatives which are intermediates for preparing senolytic agents that selectively kill senescent cells associated with numerous pathologies and diseases, including age-related pathologies and diseases.

6 Claims, No Drawings

SUGAR DERIVATIVES AND USES THEREOF TO PREPARE NOVEL SENOLYTIC AGENTS

CROSS REFERENCE TO RELATED APPLICATION

This application claims priority to U.S. Provisional Application Ser. No. 63/243,542 filed Sep. 13, 2021, under 35 U.S.C. § 119 (e) which is incorporated by reference in its entirety.

TECHNICAL FIELD

Provided herein are novel sugar derivatives which are intermediates for preparing senolytic agents that selectively kill senescent cells associated with numerous pathologies and diseases, including age-related pathologies and diseases.

BACKGROUND

Aging is a risk factor for most chronic diseases, disabilities, and declining health. Senescent cells, which are cells in replicative arrest, accumulate in aging individuals and may contribute partially or significantly to cell and tissue deterioration that underlies aging and age-related diseases (e.g., see Childs et al., Nat. Rev. Drug Discov. 16 (2017) 718-735). Cells may also become senescent after exposure to an environmental, chemical, or biological insult or as a result of disease (e.g., see Demaria et al., Cancer Discovery 7 (2017) 165-176; Schafer et al., Nat. Commun. 8 (2017) doi: 10.1038/ncomms14532).

Senolytic agents with a diverse range of pharmacologic mechanisms have been previously described in the art. The senolytic agent may be a specific inhibitor of one or more Bcl-2 anti-apoptotic protein family members where the inhibitor inhibits at least Bcl-xL (e.g., a Bcl-2/Bcl-xL/Bcl-w inhibitor; a selective Bcl-xL inhibitor; a Bcl-xL/Bcl-w inhibitor, (e.g., Navitoclax, ABT-737, A1331852, A1155463); see e.g., Childs et al., supra; Zhu et al., Aging 9 (2017) 955-965; Yosef et al., Nature Commun. (2016) doi:10.1038); an Akt kinase specific inhibitor (e.g., MK-2206); a receptor tyrosine kinase inhibitor (e.g., dasatinib, see Zhu et al., Aging Cell 14 (2015) 654-658); a CDK4/6 inhibitor (e.g., palbociclib, see Whittaker et al., Pharmacol. Ther. 173 (2017) 83-105); an mTOR inhibitor (e.g., rapamycin, see Laberge et al., Nat. Cell Biol. 17 (2015) 1049-1061); an MDM2 inhibitor (e.g., Nutlin-3, RG-7112, see U.S. Pat. Appl. 2016/0339019); an Hsp90 inhibitor (e.g., 17-DMAG, ganetespib, see Fuhrmann-Stroissnigg et al., Nat. Commun. 8 (2017) doi: 10.1038/s41467-017-00314-z); a flavone (e.g., quercetin, fisetin, see Zhu et al., Aging Cell 14 (2015) 654-658; Zhu et al., Aging 9 (2017) 955-965); or a histone deacetylase inhibitor (e.g., panobinostat, see e.g., Samaraweera et al., Sci. Rep. 7 (2017) 1900. doi: 10.1038/s41598-017-01964-1).

A significant challenge has been the identification of senolytic agents which selectively kill senescent cells while sparing non-senescent cells (see e.g., Gallop et al., U.S. Pat. No. 11,026,963). Accordingly, what is needed are novel compounds for preparing new senolytic agents which have improved selectivity for killing senescent cells while having minimal toxicity towards non-senescent cells. The novel compounds may also be converted to diagnostic agents which identify new sugars and derivatives thereof which may be incorporated in novel senolytic agents.

SUMMARY

These and other needs are satisfied by providing novel intermediates for preparing non-toxic prodrugs of senolytic agents which are activated by hydrolase enzymes that preferentially accumulate inside senescent cells.

In one aspect, a compound of Formula (I) or Formula (II):

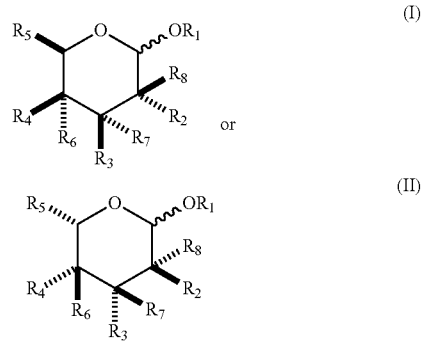

or pharmaceutically available salts, hydrate and solvates thereof is provided, where $R_1$ is —H, —$R_{15}$, —C(O)$R_{16}$ or —NH$_2$; $R_2$ is —H, —F, —OH, —OC(O)$R_9$ or —OC(O)OR$_{10}$; $R_3$ is —H, —F, —OH, —OC(O)$R_{11}$ or —OC(O)OR$_{12}$; $R_4$ is —H, —F, —OH, —OC(O)$R_{13}$ or —OC(O)OR$_{14}$; alternatively, both $R_3$ and $R_4$ together with the atoms to which they are bonded form a 5 membered cyclic acetal which is substituted by $R_{19}$ at the acetal carbon; alternatively, both $R_3$ and $R_4$ together with the atoms to which they are bonded form a 5 membered cyclic carbonate; $R_5$ is —CH$_3$, —CH$_2$OH, —OC(O)$R_{17}$ or —OC(O)OR$_{18}$; $R_6$ is —H or —F; $R_7$ is —H or —F; $R_8$ is —H or —F; $R_9$-$R_{18}$ are independently alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and $R_{19}$ is alkyl, substituted alkyl, aryl, substituted aryl, cycloalkyl, substituted cycloalkyl, cycloheteroalkyl, substituted cycloheteroalkyl, heteroaryl or substituted heteroaryl; provided that only one or two of $R_2$, $R_3$ or $R_4$ is —F; provided that $R_6$ is —F only if $R_4$ is —F, $R_7$ is —F only if $R_3$ is —F; and $R_8$ is —F only if $R_2$ is —F; provided that when $R_1$ is H and $R_5$ is —CH$_3$ and $R_3$ and $R_4$ are —OH then $R_2$ is not —H or —F; provided that when $R_1$ is H and $R_5$ is —CH$_3$ and $R_2$ and $R_4$ are —OH then $R_3$ is not —H or —F; provided that when $R_1$ is H and $R_5$ is —CH$_3$ and $R_4$—H then $R_2$ and $R_3$ are not both —OH; provided that when $R_1$ is —CH$_3$ or —C(O)CH$_3$, $R_2$ is —F and $R_5$ is —CH$_3$ then $R_3$ is not —F; provided that when $R_1$ is —CH$_3$ or —C(O)CH$_3$, $R_2$ is —F and $R_5$ is —CH$_3$ then $R_3$ and $R_4$ are not both —OH, —OC(O)Ph or —OC(O)CH$_3$; provided that when $R_1$ is —CH$_3$, $R_2$ is —F and $R_5$ is —CH$_3$ then $R_3$ is not —OC(O)CH$_3$ and $R_4$ is not —OC(O)Ph; provided that when $R_1$ is —C(O)Ph, $R_2$ is —F and $R_5$ is —CH$_3$ then $R_3$ and $R_4$ are not both —C(O)Ph; provided that when $R_1$ is —C(O)Ph, $R_4$ is —F and $R_5$ is —CH$_3$ then $R_2$ and $R_3$ are not both —C(O)Ph; provided that when $R_1$ is —C(O)CH$_3$, $R_4$ is —F and $R_5$ is —CH$_3$ then $R_2$ and $R_3$ are not both —C(O)CH$_3$; provided that when $R_1$ is —CH(CH$_3$)$_2$ or —(CH$_3$)$_3$, $R_2$ is —F and $R_5$ is —CH$_3$ then $R_3$ and $R_4$ are not both —C(O)CH$_3$; provided that when $R_1$ is —CH$_3$, $R_2$ is —H and $R_5$ is —CH$_3$ then $R_3$ and $R_4$ are not both —C(O)CH$_3$; provided that when $R_1$ is —CH$_3$, —C$_2$H$_5$, $R_3$ is —F and $R_5$ is —CH$_3$ then $R_2$ and $R_4$ are not both —OH; provided that when $R_1$ is —CH$_3$, $R_4$ is —F and $R_5$ is —CH$_3$ then $R_3$ and $R_4$ are not both —OH or —C(O)CH$_3$; provided that when $R_1$ is —$CH_3$, —$C(O)CH_3$, —$C_2H_5$, allyl, octyl or dodecyl, $R_2$ is —F and $R_5$ is —$CH_2OH$ or —$OC(O)R_{17}$ then $R_3$ and $R_4$ are not both —OH; provided that when $R_1$ is —$CH_3$, $R_2$ is —F and $R_5$ is —$CH_2OH$ or —$OC(O)R_{17}$ then $R_3$ and $R_4$ are not both —$C(O)Ph$ or —$C(O)CH_3$; provided that when $R_1$ is —$CH_3$, octyl, dodecyl, $R_3$ is —F and $R_5$ is —$CH_2OH$ or —$OC(O)R_{17}$ then $R_2$ and $R_4$ are not both —OH; provided that when $R_1$ is —$CH_3$, $R_3$ is —F and $R_5$ is —$CH_2OH$ or —$OC(O)R_{17}$ then $R_2$ and $R_4$ are not both —$OC(O)CH_3$ or —$C(O)Ph$; provided that when $R_1$ is —$CH_3$, $R_4$ is —F and $R_5$ is —$CH_2OH$ or —$OC(O)R_{17}$ then $R_2$ and $R_3$ are not both —OH.

In another aspect, a compound of Formula (III) or Formula (IV):

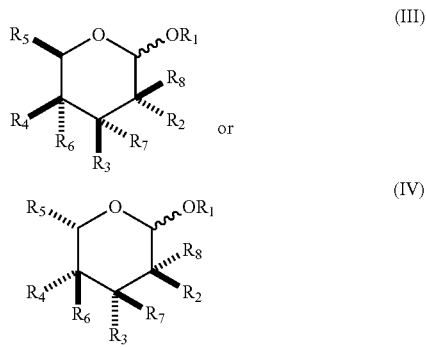

or pharmaceutically available salts, hydrate and solvates thereof is provided, where $R_1$ is —H, —$R_{15}$, —$NH_2$ or —$C(O)R_{16}$; $R_2$ is —H, —F, —OH, —$OC(O)R_9$ or —$OC(O)OR_{10}$; $R_3$ is —H, —F, —OH, —$OC(O)R_{11}$ or —$OC(O)OR_{12}$; $R_4$ is —H, —F, —OH, —$OC(O)R_{13}$ or —$OC(O)OR_{14}$; alternatively, both $R_3$ and $R_4$ together with the atoms to which they are bonded form a 5 membered cyclic acetal which is substituted by $R_{19}$ at the acetal carbon; alternatively, both $R_3$ and $R_4$ together with the atoms to which they are bonded form a 5 membered cyclic carbonate; $R_5$ is —$CH_2F$, —$CHF_2$ or —$CF_3$; $R_6$ is —H or —F; $R_7$ is —H or —F; $R_8$ is —H or —F; $R_9$-$R_{16}$ are independently alkyl, alkenyl, alkynyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and $R_{19}$ is alkyl, substituted alkyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; optionally one of $R_2$, $R_3$ or $R_4$ is —F; provided that $R_6$ is —F only if $R_4$ is —F; $R_7$ is —F only if $R_3$ is —F; and $R_8$ is —F only if $R_2$ is —F; provided that when $R_1$ is H, then $R_2$, $R_3$ and $R_4$ are not all —OH; provided that when $R_1$ is H or phenyl, $R_5$ is —$CH_2F$ and $R_4$ is —F, then $R_2$ and $R_3$ are not both —OH; provided that when $R_1$ is —$CH_3$, —$C_2H_5$ allyl, octyl, dodecyl or substituted phenyl and $R_5$ is —$CH_2F$, then $R_2$, $R_3$ and $R_4$ are not —OH; provided that when $R_1$ is —$CH_3$ or allyl, $R_5$ is —$CH_2F$ and $R_4$ is —OH then, then $R_2$ and $R_3$ are not —$C(O)Ph$; provided that when $R_1$ is —$CH_3$, allyl, —$C(O)CH_3$, dodecyl, substituted phenyl and $R_5$ is —$CH_2F$, then $R_2$, $R_3$ and $R_4$ are not —$C(O)CH_3$; provided that when $R_1$ is —$C(O)CH_3$ and $R_5$ is —$CHF_2$, then $R_2$, $R_3$ and $R_4$ are not —$C(O)CH_3$; provided that when $R_1$ is —$C(O)CH_3$ and $R_5$ is —$CF_3$, then $R_2$, $R_3$ and $R_4$ are not —$C(O)CH_3$; provided that when $R_1$ is —$CH_3$, —$C(O)Ph$, or allyl and $R_5$ is —$CH_2F$, then $R_2$, $R_3$ and $R_4$ are not —$C(O)Ph$; provided that when $R_1$ is —$CH_3$ or allyl, $R_5$ is —$CH_2F$ and $R_4$ is —OH then $R_2$ and $R_3$ are not both —$C(O)Ph$; provided that when $R_1$ is substituted phenyl, $R_5$ is —$CH_2F$, $R_3$ and $R_4$ are —F then $R_2$ is not —OH; provided that when $R_1$ is H, —$C(O)CH_3$ or —$CH_2CH_2OH$ and $R_5$ is —$CH_2F$ and $R_4$ is —F, then $R_2$ and $R_3$ are not —$C(O)CH_3$; provided that when $R_1$ is —$C(O)CH_3$ and $R_5$ is —$CH_2F$, then $R_2$, $R_3$ and $R_4$ are not all —$C(O)Ph$; provided that when $R_1$ and $R_4$ are —$C(O)CH_3$ and $R_5$ is —$CH_2F$, then $R_2$ and $R_3$ are not —$C(O)Ph$; provided that when $R_1$ is —$C(O)Ph$ and $R_5$ is —$CH_2F$, then $R_2$, $R_3$ and $R_4$ are not —$C(O)Ph$; provided that when $R_1$ is —$C(O)Ph$ where the phenyl is substituted with —$CO_2CH_3$ and $R_5$ is —$CH_2F$, then $R_2$, $R_3$ and $R_4$ are not —$C(O)CH_3$.

DETAILED DESCRIPTION

Definitions

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

A dash ("-") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. It should be understood that u to v carbons includes u+1 to v, u+2 to v, u+3+v, etc. carbons, u+1 to u+3 to v, u+1 to u+4 to v, u+2 to u+4 to v, etc. and cover all possible permutation of u and v.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyl; propyls such as propan-1-yl, propan-2-yl, etc.; butyls such as butan-1-yl, butan-2-yl, 2-methyl-propan-1-yl, 2-methyl-propan-2-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, an alkenyl group comprises from 1 to 20 carbon atoms ($C_1$-$C_{20}$ alkenyl). Inn other embodiments, an alkenyl group comprises from 1 to 10 carbon atoms ($C_1$-$C_{10}$ alkenyl). In still other embodiments, an alkenyl group comprises from 1 to 6 carbon atoms ($C_1$-$C_6$ alkenyl).

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, an alkynyl group comprises from 1 to 20 carbon atoms ($C_1$-$C_{20}$ alkynyl). In other embodiments, an alkynyl group comprises from 1 to 10 carbon atoms ($C_1$-$C_{10}$ alkynyl). In still other embodiments, an alkynyl group comprises from 1 to 6 carbon atoms ($C_1$-$C_6$ alkynyl).

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In some embodiments, an arylalkyl group is ($C_6$-$C_{30}$) arylalkyl, e.g., the alkyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkyl moiety of the arylalkyl group is ($C_1$-$C_5$) alkyl and the aryl moiety is ($C_6$-$C_{10}$) aryl.

"Arylalkenyl," by itself or as part of another substituent, refers to an acyclic alkenyl group in which one of the hydrogen atoms bonded to a carbon atom, is replaced with an aryl group as, as defined herein. In some embodiments, an arylalkenyl group is ($C_6$-$C_{30}$) arylalkenyl, e.g., the alkenyl moiety of the arylalkenyl group is ($C_1$-$C_{10}$) alkenyl and the aryl moiety is ($C_6$-$C_{20}$) aryl. In other embodiments, an arylalkenyl group is ($C_6$-$C_{20}$) arylalkenyl, e.g., the alkenyl moiety of the arylalkenyl group is ($C_1$-$C_8$) alkenyl and the aryl moiety is ($C_6$-$C_{12}$) aryl. In still other embodiments, an arylalkenyl group is ($C_6$-$C_{15}$) arylalkenyl, e.g., the alkenyl moiety of the arylalkenyl group is ($C_1$-$C_5$) alkenyl and the aryl moiety is ($C_6$-$C_{10}$) aryl.

"Arylalkynyl," by itself or as part of another substituent, refers to an acyclic alkynyl group in which one of the hydrogen atoms bonded to a carbon atom, is replaced with an aryl group as, as defined herein. In some embodiments, an arylalkynyl group is ($C_6$-$C_{30}$) arylalkynyl, e.g., the alkynyl moiety of the arylalkynyl group is ($C_1$-$C_{10}$) alkynyl and the aryl moiety is ($C_6$-$C_{20}$) aryl. In other embodiments, an arylalkynyl group is ($C_6$-$C_{20}$) arylalkynyl, e.g., the alkynyl moiety of the arylalkenyl group is ($C_1$-$C_8$) alkynyl and the aryl moiety is ($C_6$-$C_{12}$) aryl. In still other embodiments, an arylalkynyl group is ($C_6$-$C_{15}$) arylalkynyl, e.g., the alkynyl moiety of the arylalkynyl group is ($C_1$-$C_5$) alkynyl and the aryl moiety is ($C_6$-$C_{10}$) aryl.

"Cycloalkyl," by itself or as part of another substituent, refers to a saturated cyclic monovalent hydrocarbon radical derived by the removal of one hydrogen atom from a single carbon atom of a parent cycloalkane. Typical cycloalkyl groups include, but are not limited to, cyclopropyl, cyclobutyl, cyclopentyl cycopentenyl; etc.; and the like. In some embodiments, a cycloalkyl group comprises from 3 to 20 carbon atoms ($C_1$-$C_{15}$ cycloalkyl). In other embodiments, a cycloalkyl group comprises from 3 to 10 carbon atoms ($C_1$-$C_{10}$ cycloalkyl). In still other embodiments, a cycloalkyl group comprises from 3 to 8 carbon atoms ($C_1$-$C_8$ cycloalkyl). The term "cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Cycloalkenyl," by itself or as part of another substituent, refers to an unsaturated cyclic monovalent hydrocarbon radical derived by the removal of one hydrogen atom from a single carbon atom of a parent cycloalkene. Typical cycloalkenyl groups include, but are not limited to, cyclopropene, cyclobutene cyclopentene; etc.; and the like. In some embodiments, a cycloalkenyl group comprises from 3 to 20 carbon atoms ($C_1$-$C_{20}$ cycloalkenyl). In other embodiments, a cycloalkenyl group comprises from 3 to 10 carbon atoms ($C_1$-$C_{10}$ cycloalkenyl). In still other embodiments, a cycloalkenyl group comprises from 3 to 8 carbon atoms ($C_1$-$C_8$ cycloalkenyl). The term "cyclic monovalent hydrocarbon radical" also includes multicyclic hydrocarbon ring systems having a single radical and between 3 and 12 carbon atoms.

"Cycloheteroalkyl," by itself or as part of another substituent, refers to a cycloalkyl group as defined herein in which one or more one or more of the carbon atoms (and optionally any associated hydrogen atoms), are each, independently of one another, replaced with the same or different heteroatoms or heteroatomic groups as defined in "heteroalkyl" below. In some embodiments, a cycloheteroalkyl group comprises from 3 to 20 carbon and hetero atoms ($_{1\text{-}20}$ cycloheteroalkyl). In other embodiments, a cycloheteroalkyl group comprises from 3 to 10 carbon and hetero atoms ($_{1\text{-}10}$ cycloheteroalkyl). In still other embodiments, a cycloheteroalkyl group comprises from 3 to 8 carbon and hetero atoms (1.8 cycloheteroalkyl). The term "cyclic monovalent heteroalkyl radical" also includes multicyclic heteroalkyl ring systems having a single radical and between 3 and 12 carbon and at least one hetero atom.

"Cycloheteroalkenyl," by itself or as part of another substituent, refers to a cycloalkenyl group as defined herein in which one or more one or more of the carbon atoms (and optionally any associated hydrogen atoms), are each, independently of one another, replaced with the same or different heteroatoms or heteroatomic groups as defined in "heteroalkenyl" below. In some embodiments, a cycloheteroalkenyl group comprises from 3 to 20 carbon and hetero atoms ($_{1\text{-}20}$ cycloheteroalkenyl). In other embodiments, a cycloheteroalkenyl group comprises from 3 to 10 carbon and hetero atoms ($_{1\text{-}10}$) cycloheteroalkenyl). In still other embodiments, a cycloheteroalkenyl group comprises from 3 to 8 carbon and heteroatoms ($_{1\text{-}8}$ cycloheteroalkenyl). The term "cyclic monovalent heteroalkenyl radical" also includes multicyclic heteroalkenyl ring systems having a single radical and between 3 and 12 carbon and at least one hetero atoms.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," refer to an alkyl, group, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some embodiments, an heteroalkyl group comprises from 1 to 20 carbon and hetero atoms (1-20 heteroalkyl). In other embodiments, an heteroalkyl group comprises from 1 to 10 carbon and hetero atoms ($_{1\text{-}10}$ heteroalkyl). In still other embodiments, an heteroalkyl group comprises from 1 to 6 carbon and hetero atoms ($_1$-6 heteroalkyl).

"Heteroalkenyl," refers to an alkenyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some embodiments, an heteroalkenyl group comprises from 1 to 20 carbon and hetero atoms ($_{1\text{-}20}$ heteroalkenyl). In other embodiments, an heteroalkenyl group comprises from 1 to 10 carbon and hetero atoms ($_{1\text{-}10}$ heteroalkenyl). In still other embodiments, an heteroalkenyl group comprises from 1 to 6 carbon and hetero atoms ($_{1\text{-}6}$ heteroalkenyl).

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or $sp^3$ carbon atom, is replaced with a heteroaryl group. In some embodiments, the heteroarylalkyl group is a 6-21 membered heteroarylalkyl, e.g., the alkyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkyl moiety is ($C_1$-$C_3$) alkyl and the heteroaryl moiety is a 5-10 membered heteroaryl.

"Heteroarylalkenyl," by itself or as part of another substituent refers to an acyclic alkenyl group in which one of the hydrogen atoms bonded to a carbon atom, is replaced with a heteroaryl group. In some embodiments, the heteroarylalkenyl group is a 6-21 membered heteroarylalkyl, e.g., the alkenyl moiety of the heteroarylalkenyl is ($C_1$-$C_6$) alkenyl and the heteroaryl moiety is a 5-15-membered heteroaryl. In other embodiments, the heteroarylalkenyl is a 6-13 membered heteroarylalkenyl, e.g., the alkenyl moiety is ($C_1$-$C_3$) alkyl and the heteroaryl moiety is a 5-10 membered heteroaryl.

"Heteroarylalkynyl," by itself or as part of another substituent refers to an acyclic alkenyl group in which one of the hydrogen atoms bonded to a carbon atom, is replaced with a heteroaryl group. In some embodiments, the heteroarylalkynyl group is a 6-21 membered heteroarylalkyl, e.g., the alkynyl moiety of the heteroarylalkynyl is ($C_1$-$C_6$) alkynyl and the heteroaryl moiety is a 5-15-membered heteroaryl. In other embodiments, the heteroarylalkynyl is a 6-13 membered heteroarylalkynyl, e.g., the alkynyl moiety is ($C_1$-$C_3$) alkyl and the heteroaryl moiety is a 5-10 membered heteroaryl.

"Hydrates," refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routinely offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System," refers to an unsaturated cyclic or polycyclic ring system having a conjugated p electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, b-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Prodrug" as used herein, refers to a derivative of a drug molecule that requires a transformation within the body to release the active drug. Prodrugs are frequently, although not necessarily, pharmacologically inactive until converted to the parent drug.

"Promoiety" as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Senescence" or "senescent cells" as used herein, refers to a state wherein cells have acquired one or more markers for senescence in response to some cellular stress. Such markers may typically include permanent withdrawal from the cell cycle, the expression of a bioactive secretome of inflammatory factors, altered methylation, senescence-associated heterochromatin foci (SAHF), expression markers for oxidative stress, expression of markers for DNA damage, protein and lipid modifications, morphological features of senescence, altered lysosome/vacuoles and expression of senescence-associated b-galactosidase (see Lorenzo Galluzzi et al. (eds.), Cell Senescence: Methods and Protocols, Methods in Molecular Biology, vol. 965, DOI 10.1007/978-1-62703-239-1_4, © Springer Science+Business Media, LLC 2013).

"Senolytic agent" as used herein refers to an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill a non-senescent cell in a clinically significant or biologically significant manner. In certain embodiments, the senolytic agents described herein alter at least one signaling pathway in a manner that induces (i.e., initiates, stimulates, triggers, activates, promotes) and results in death of the senescent cell.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205208 in *Polymorphism in Pharmaceutical Solids*, (Brittain, H. ed.), Marcel Dekker, Inc., New York, NY, 1999)). The above methods for preparing solvates are well within the ambit of those of skill in the art, are completely conventional and do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holo-diag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $R^a$, halo, $-O^-$, $=O$, $-OR^b$, $-SR^b$, $-S^-$, $=S$, $-NR^cR^c$, $-NR^b$, $=N-OR^b$, trihalomethyl, $-CF_3$, $-CN$, $-OCN$, $-SCN$, $-NO$, $-NO_2$, $-N-OR^b$, $-N-NR^cR^c$, $-NR^bS(O)_2R^b$, $=N_2$, $-N_3$, $-S(O)_2R^b$, $-S(O)_2NR^bR^b$, $-S(O)_2O^-$, $-S(O)_2OR^b$, $-OS(O)_2R^b$, $-OS(O)_2O^-$, $-OS(O)_2OR^b$, $-OS(O)_2NR^cNR^c$, $-P(O)(O^-)_2$, $-P(O)(OR^b)(O)$, $-P(O)(OR^b)(OR^b)$, $-C(O)R^b$, $-C(O)NR^b-OR^b-C(S)\ R^b$, $-C(NR^b)R^b$, $-C(O)O^-$, $-C(O)OR^b$, $-C(S)OR^b$, $-C(O)NR^cR^c$, $-C(NR^b)NR^cR^c$, $-OC(O)R^b$, $-OC(S)\ R^b$, $-OC(O)O^-$, $-OC(O)OR^b$, $-OC(O)NR^cR^c$, $-OC(NCN)NR^cR^c-OC(S)OR^b$, $-NR^bC(O)R^b$, $-NR^bC(S)R^b$, $-NR^bC(O)O-$, $-NR^bC(O)OR^b$, $-NR^bC(NCN)OR^b$, $-NR^bS(O)_2NR^cR^c$, $-NR^bC(S)OR^b$, $-NR^bC(O)NR^cR^c$, $-NR^bC(S)NR^cR^c$, $-NR^bC(S)NR^bC(O)R^a$, $-NR^bS(O)_2OR^b$, $-NR^bS(O)_2R^b$, $-NR^bC(NCN)\ NR^cR^c$, $-NR^bC(NR^b)R^b$ and $-NR^bC(NR^b)NR^cR^c$, where each $R^a$ is independently, aryl, substituted aryl, heteroalkyl, substituted heteroalkyl, heteroaryl or substituted heteroaryl; each $R^b$ is independently hydrogen, alkyl, heteroalkyl, substituted heteroalkyl, arylalkyl, substituted arylalkyl, heteroarylalkyl or substituted heteroarylalkyl; and each R is independently $R^b$ or alternatively, the two $R^c$s taken together with the nitrogen atom to which they are bonded form a 4-, 5-, 6- or 7 membered-cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, $-NR^cR^c$ is meant to include $-NH_2$, $-NH$-alkyl, N-pyrrolidinyl and N-morpholinyl. In other embodiments, substituent groups useful for substituting saturated carbon atoms in the specified group or radical include $R^a$, halo, $-OR^b$, $-NR^cR^c$, trihalomethyl, $-CN$, $-NR^bS(O)_2R^b$, $-C(O)R^b$, $-C(O)NR^b-OR^b$, $-C(O)OR^b$, $-C(O)NR^cR^c$, $-OC(O)R^b$, $-OC(O)OR^b$, $-OS(O)_2NR^cNR^c$, $-OC(O)NR^cR^c$, and $-NR^bC(O)OR^b$, where each $R^a$ is independently alkyl, aryl, heteroaryl, each $R^b$ is independently hydrogen, $R^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6 or -7 membered-cycloheteroalkyl ring.

Substituent groups useful for substituting unsaturated carbon atoms in the specified group or radical include —$R^a$, halo, —O⁻, —$OR^b$, —$SR^b$, —S⁻, —$NR^cR^c$, trihalomethyl, —$CF_3$, —CN, —OCN, —SCN, —NO, —$NO_2$, —$N_3$, —$S(O)_2O^-$, —$S(O)_2OR^b$, —$OS(O)_2R^b$, —$OS(O)_2OR^b$, —$OS(O)_2O^-$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —OC(O) O⁻, —OC(O)$OR^b$, —$OC(S)OR^b$, —$OC(O)NR^cR^c$, —$OS(O)_2NR^cNR^c$, —$NR^bC(O)R^b$, —$NR^bC(S)R^b$, —$NR^bC(O)O^-$, —$NR^bC(O)OR^b$, —$NR^bS(O)_2OR^a$, —$NR^bS(O)_2R^a$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. In other embodiments, substituent groups useful for substituting unsaturated carbon atoms in the specified group or radical include —$R^a$, halo, —$OR^b$, —$SR^b$, —$NR^cR^c$, trihalomethyl, —CN, —$S(O)_2OR^b$, —$C(O)R^b$, —$C(O)OR^b$, —$C(O)NR^cR^c$, —$OC(O)R^b$, —$OC(O)OR^b$, —$OS(O)_2NR^c$-$NR^c$, —$NR^bC(O)R^b$ and —$NR^bC(O)OR^b$, where $R^a$, $R^b$ and $R^c$ are as previously defined.

Substituent groups useful for substituting nitrogen atoms in heteroalkyl and cycloheteroalkyl groups include, but are not limited to, —$R^a$, —O⁻, —$OR^b$, —$SR^b$, —S⁻, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$, $R^b$ and $R^c$ are as previously defined. In some embodiments, substituent groups useful for substituting nitrogen atoms in heteroalkyl and cycloheteroalkyl groups include, $R^a$, halo, —$OR^b$, —$NR^cR^c$, trihalomethyl, —CN, —$S(O)_2OR^b$, —$OS(O)_2R^b$, —$OS(O)_2OR^b$, —$C(O)R^b$, —$C(NR^b)R^b$, —$C(O)OR^b$, —$C(O)NR^cR^c$, —$OC(O)R^b$, —$OC(O)OR^b$, —$OS(O)_2NR^cNR^c$, —$NR^bC(O)R^b$ and —$NR^bC(O)OR^b$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Senolytic agent" as used herein refers to an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill a non-senescent cell in a clinically significant or biologically significant manner. In certain embodiments, the senolytic agents described herein alter at least one signaling pathway in a manner that induces (i.e., initiates, stimulates, triggers, activates, promotes) and results in death of the senescent cell.

Reference will now be made in detail to particular embodiments of compounds and methods. The disclosed embodiments are not intended to be limiting of the claims. To the contrary, the claims are intended to cover all alternatives, modifications and equivalents.

Novel Synthetic Intermediates

Provided herein are novel compounds which may be incorporated in novel senolytic agents (see co-pending U.S. patent application Ser. No. 17/943,824) and novel diagnostic agents (see co-pending U.S. patent application Ser. No. 17/943,836). The novel senolytic agents may have improved selectivity for killing senescent cells while having minimal toxicity towards non-senescent cells. The novel diagnostic agents may identify novel sugars which may be incorporated into novel senolytic agents In one aspect, a compound of Formula (I) or Formula (II):

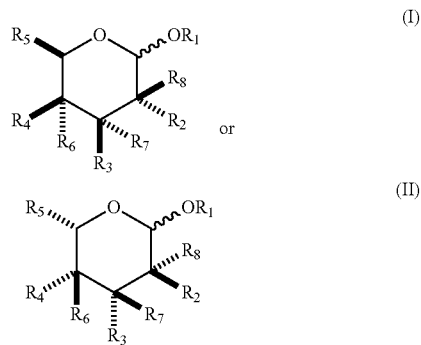

or pharmaceutically available salts, hydrate and solvates thereof is provided, wherein: $R_1$ is —H, —$R_{15}$, —$C(O)R_{16}$ or —$NH_2$; $R_2$ is —H, —F, —OH, —$OC(O)R_9$ or —$OC(O)OR_{10}$; $R_3$ is —H, —F, —OH, —$OC(O)R_{11}$ or —$OC(O)OR_{12}$; $R_4$ is —H, —F, —OH, —$OC(O)R_{13}$ or —$OC(O)OR_{14}$; alternatively, both $R_3$ and $R_4$ together with the atoms to which they are bonded form a 5 membered cyclic acetal which is substituted by $R_{19}$ at the acetal carbon; alternatively, both $R_3$ and $R_4$ together with the atoms to which they are bonded form a 5 membered cyclic carbonate; $R_5$ is —$CH_3$, —$CH_2OH$, —$OC(O)R_{17}$ or —$OC(O)OR_{18}$; $R_6$ is —H or —F; $R_7$ is —H or —F; $R_8$ is —H or —F; $R_9$-$R_{18}$ are independently alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and $R_{19}$ is alkyl, substituted alkyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl provided that only one or two of $R_2$, $R_3$ or $R_4$—F; provided that $R_6$ is —F only if $R_4$ is —F, $R_7$ is —F only if $R_3$ is —F; and $R_8$ is —F only if $R_2$ is —F; provided that when $R_1$ is H and $R_5$ is —$CH_3$ and $R_3$ and $R_4$ are —OH then $R_2$ is not —H or —F; provided that when $R_1$ is H and $R_5$ is —$CH_3$ and $R_2$ and $R_4$ are —OH then $R_3$ is not —H or —F; provided that when $R_1$ is H and $R_5$ is —$CH_3$ and $R_4$—H then $R_2$ and $R_3$ are not both —OH; provided that when $R_1$ is —$CH_3$ or —$C(O)CH_3$, $R_2$ is —F and $R_5$ is —$CH_3$ then $R_3$ is not —F; provided that when $R_1$ is —$CH_3$ or —$C(O)CH_3$, $R_2$ is —F and $R_5$ is —$CH_3$ then $R_3$ and $R_4$ are not both —OH, —OC(O)Ph or —OC(O)$CH_3$; provided that when $R_1$ is —$CH_3$, $R_2$ is —F and $R_5$ is —$CH_3$ then $R_3$ is not —OC(O)$CH_3$ and $R_4$ is not-OC(O)Ph; provided that when $R_1$ is —C(O)Ph, $R_2$ is —F and $R_5$ is —$CH_3$ then $R_3$ and $R_4$ are not both —C(O)Ph; provided that when $R_1$ is —C(O)Ph, $R_4$ is —F and $R_5$ is —$CH_3$ then $R_2$ and $R_3$ are not both —C(O)Ph; provided that when $R_1$ is —C(O)$CH_3$, $R_4$ is —F and $R_5$ is —$CH_3$ then $R_2$ and $R_3$ are not both —C(O)$CH_3$; provided that when $R_1$ is —CH($CH_3$)$_2$ or —($CH_3$)$_3$, $R_2$ is —F and $R_5$ is —$CH_3$ then $R_3$ and $R_4$ are not both —C(O)$CH_3$; provided that when $R_1$ is —$CH_3$, $R_2$ is —H and $R_5$ is —$CH_3$ then $R_3$ and $R_4$ are not both —C(O)$CH_3$; provided that when $R_1$ is —$CH_3$, —$C_2H_5$, $R_3$ is —F and $R_5$ is —$CH_3$ then $R_2$ and $R_4$ are not both —OH; provided that when $R_1$ is —$CH_3$, $R_4$ is —F and $R_5$ is —$CH_3$ then $R_3$ and $R_4$ are not both —OH or —C(O)$CH_3$; provided that when $R_1$ is —$CH_3$, —C(O)$CH_3$, —$C_2H_5$, allyl, octyl or dodecyl, $R_2$ is —F and $R_5$ is —$CH_2$OH or —OC(O)$R_{17}$ then $R_3$ and $R_4$ are not both —OH; provided that when $R_1$ is —$CH_3$, $R_2$ is —F and $R_5$ is —$CH_2$OH or —OC(O)$R_{17}$ then $R_3$ and $R_4$ are not both —C(O)Ph or —C(O)$CH_3$; provided that when $R_1$ is —$CH_3$, octyl, dodecyl, $R_3$ is —F and $R_5$ is —$CH_2$OH or —OC(O)$R_{17}$ then $R_2$ and $R_4$ are not both —OH; provided that when $R_1$ is —$CH_3$, $R_3$ is —F and $R_5$ is —$CH_2$OH or —OC(O)$R_{17}$ then $R_2$ and $R_4$ are not both —OC(O)$CH_3$ or —C(O)Ph; provided that when $R_1$ is —$CH_3$, $R_4$ is —F and $R_5$ is —$CH_2$OH or —OC(O)$R_{17}$ then $R_2$ and $R_3$ are not both —OH.

In some embodiments, $R_1$ is not —$CH_3$, allyl —C(O)$CH_3$, —C(O)Ph, —$C_2H_5$, octyl, —CH($CH_3$)$_2$, —($CH_3$)$_3$, or dodecyl. In other embodiments, $R_1$ is not —H.

In some embodiments, $R_2$ is —H or —F and $R_3$ is —H or —F. In other embodiments, $R_2$ is —H or —F and $R_4$ is —H or —F.

In some embodiments, $R_3$ is —H or —F and $R_4$ is —H or —F. In other embodiments, $R_2$ is —H or —F, $R_3$ is —F and $R_7$ is —F. In other embodiments, $R_2$ is —H or —F, $R_4$ is —F and $R_6$ is —F. In still other embodiments, $R_3$ is —H or —F, $R_4$ is —F and $R_6$ is —F. In still other embodiments, $R_2$ is —F, $R_8$ is —F and $R_3$ is —H or —F. In still other embodiments, $R_2$ is —F, $R_8$ is —F and $R_4$ is —H or —F. In still other embodiments, $R_3$ is —F, $R_7$ is —F and $R_4$ is —H or —F.

In some embodiments, $R_2$ is —F and $R_8$ is —F. In other embodiments, $R_3$ is —F and $R_7$ is —F. In still other embodiments, $R_4$ is —F and $R_6$ is —F.

In some embodiments, $R_2$ is —H or —F. In other embodiments, $R_3$ is —H or —F. In still other embodiments, $R_4$ is —H or —F.

In some embodiments, $R_9$-$R_{19}$ are independently alkyl, alkenyl, aryl, substituted aryl, cycloalkyl, or cycloheteroalkyl. In other embodiments, $R_9$-$R_{19}$ are independently ($C_1$-$C_4$) alkyl, ($C_1$-$C_4$) alkenyl, phenyl, substituted phenyl, ($C_5$-$C_7$) cycloalkyl or ($C_5$-$C_7$) cycloheteroalkyl.

In some of the above embodiments, $R_1$ is —H. In some other of the above embodiments, $R_1$ is —$CH_3$. In still some other of the above embodiments, $R_1$ is —C(O)$CH_3$ or —C(O)Ph.

In another aspect, a compound of Formula (III) or Formula (IV):

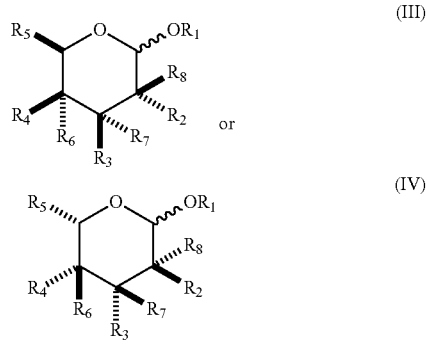

or pharmaceutically available salts, hydrate and solvates thereof is provided, wherein: $R_1$ is —H, —$R_{15}$, —$NH_2$ or —C(O)$R_{16}$; $R_2$ is —H, —F, —OH, —OC(O)$R_9$ or —OC(O)O$R_{10}$; $R_3$ is —H, —F, —OH, —OC(O)$R_{11}$ or —OC(O)O$R_{12}$; $R_4$ is —H, —F, —OH, —OC(O)$R_{13}$ or —OC(O)O$R_{14}$; alternatively, both $R_3$ and $R_4$ together with the atoms to which they are bonded form a 5 membered cyclic acetal which is substituted by $R_{19}$ at the acetal carbon; alternatively, both $R_3$ and $R_4$ together with the atoms to which they are bonded form a 5 membered cyclic carbonate; $R_5$ is —$CH_2$F, —$CHF_2$ or —$CF_3$; $R_6$ is —H or —F; $R_7$ is —H or —F; $R_8$ is —H or —F; $R_9$-$R_{16}$ are independently alkyl, alkenyl, alkynyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and $R_{19}$ is alkyl, substituted alkyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl optionally one of $R_2$, $R_3$ or $R_4$ is —H or —F; provided that $R_6$ is —F only if $R_4$ is —F; $R_7$ is —F only if $R_3$ is —F; and $R_8$ is —F only if $R_2$ is —F; provided that when $R_1$ is H, then $R_2$, $R_3$ and $R_4$ are not all —OH; provided that when $R_1$ is H or phenyl, $R_5$ is —$CH_2$F and $R_4$ is —F, then $R_2$ and $R_3$ are not both —OH; provided that when $R_1$ is —$CH_3$, —$C_2H_5$ allyl, octyl, dodecyl or substituted phenyl and $R_5$ is —$CH_2$F, then $R_2$, $R_3$ and $R_4$ are not —OH; provided that when $R_1$ is —$CH_3$ or allyl, $R_5$ is —$CH_2$F and $R_4$ is —OH then, then $R_2$ and $R_3$ are not —C(O)Ph; provided that when $R_1$ is —$CH_3$, allyl, —C(O)$CH_3$, dodecyl, substituted phenyl and $R_5$ is —$CH_2$F, then $R_2$, $R_3$ and $R_4$ are not —C(O)$CH_3$; provided that when $R_1$ is —C(O)$CH_3$ and $R_5$ is —$CHF_2$, then $R_2$, $R_3$ and $R_4$ are not —C(O)$CH_3$; provided that when $R_1$ is —C(O)$CH_3$ and $R_5$ is —$CF_3$, then $R_2$, $R_3$ and $R_4$ are not —C(O)$CH_3$; provided that when $R_1$ is —$CH_3$, —C(O)Ph, or allyl and $R_5$ is —$CH_2$F, then $R_2$, $R_3$ and $R_4$ are not —C(O)Ph; provided that when $R_1$ is —$CH_3$ or allyl, $R_5$ is —$CH_2$F and $R_4$ is —OH then $R_2$ and $R_3$ are not both —C(O)Ph; provided that when $R_1$ is substituted phenyl, $R_5$ is —$CH_2$F, $R_3$ and $R_4$ are —F then $R_2$ is not —OH; provided that when $R_1$ is H, —C(O)$CH_3$ or —$CH_2CH_2$OH and $R_5$ is —$CH_2$F and $R_4$ is —F, then $R_2$ and $R_3$ are not —C(O)$CH_3$; provided that when $R_1$ is —C(O)$CH_3$ and $R_5$ is —$CH_2$F, then $R_2$, $R_3$ and $R_4$ are not all —C(O)Ph; provided that when $R_1$ and $R_4$ are —C(O)$CH_3$ and $R_5$ is —$CH_2$F, then $R_2$ and $R_3$ are not —C(O)Ph; provided that when $R_1$ is —C(O)Ph and $R_5$ is —$CH_2F$, then $R_2$, $R_3$ and $R_4$ are not —C(O)Ph; provided that when $R_1$ is —C(O)Ph where the phenyl is substituted with —$CO_2CH_3$ and $R_5$ is —$CH_2F$, then $R_2$, $R_3$ and $R_4$ are not —C(O)$CH_3$.

In some embodiments, $R_1$ is not —$CH_3$, —C(O)$CH_3$, allyl, octyl, dodecyl or substituted phenyl when $R_5$ is —$CH_2F$. In other embodiments, $R_1$ is not —$CH_3$, —C(O)Ph, —C(O)$CH_3$, allyl, octyl, dodecyl or substituted phenyl. In still other embodiments, $R_1$ is not —H.

In some embodiments, $R_2$ is —H or —F and $R_3$ is —H or —F. In other embodiments, $R_2$ is —H or —F and $R_4$ is —H or —F. In still other embodiments, $R_3$ is —H or —F and $R_4$ is —H or —F.

In some embodiments, $R_2$ is —H or —F, $R_3$ is —F and $R_7$ is —F. In other embodiments, $R_2$ is —H or —F, $R_4$ is —F and $R_6$ is —F. In still other embodiments, $R_3$ is —H or —F, $R_4$ is —F and $R_6$ is —F.

In some embodiments, $R_2$ is —F, $R_8$ is —F and $R_3$ is —H or —F. In other embodiments, $R_2$ is —F, $R_8$ is —F and $R_4$ is —H or —F. In still other embodiments, $R_3$ is —F, $R_7$ is —F and $R_4$ is —H or —F.

In some embodiments, $R_2$ is —F and $R_8$ is —F. In other embodiments, $R_3$ is —F and $R_7$ is —F. In still other embodiments, $R_4$ is —F and $R_6$ is —F.

In some embodiments, $R_2$ is —H or —F. In other embodiments, $R_3$ is —H or —F. In still other embodiments, $R_4$ is —H or —F.

In some embodiments, $R_9$-$R_{16}$ and $R_{19}$ are independently alkyl, alkenyl, aryl, substituted aryl, cycloalkyl or cycloheteroalkyl. In other embodiments, $R_9$-$R_{16}$ and $R_{19}$ are independently ($C_1$-$C_4$) alkyl, ($C_1$-$C_4$) alkenyl, phenyl, substituted phenyl, ($C_5$-$C_7$) cycloalkyl or ($C_5$-$C_7$) cycloheteroalkyl.

In some of the above embodiments, $R_1$ is —H. In some other of the above embodiments, $R_1$ is —$CH_3$. In still some other of the above embodiments, $R_1$ is —C(O)$CH_3$ or —C(O)Ph.

Exemplary compounds are shown in Table 1 below.

TABLE 1

| Structure | No. |
|---|---|
| (structure) | 211 |
| (structure) | 217 |
| (structure) | 222 |
| (structure) | 223 |

TABLE 1-continued

| Structure | No. |
|---|---|
| (structure) | 227 |
| (structure) | 228 |
| (structure) | 229 |
| (structure) | 230 |
| (structure) | 234 |
| (structure) | 236 |
| (structure) | 239 |
| (structure) | 242 |

TABLE 1-continued

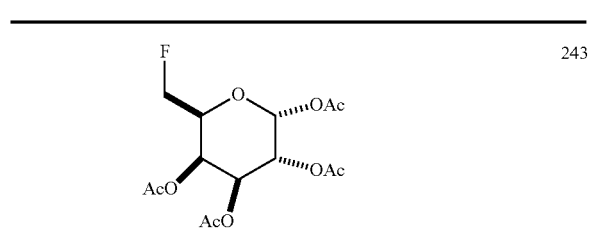
243

Compounds of Formula (I) and (II) may be prepared by conventional methods well known to the artisan skilled in carbohydrate chemistry. Exemplary methods of synthesis of the compounds described herein can be found in Schemes 1-8 in the experimental section.

The following examples are provided for illustrative purposes only and are not intended to limit the scope of the invention.

EXAMPLES

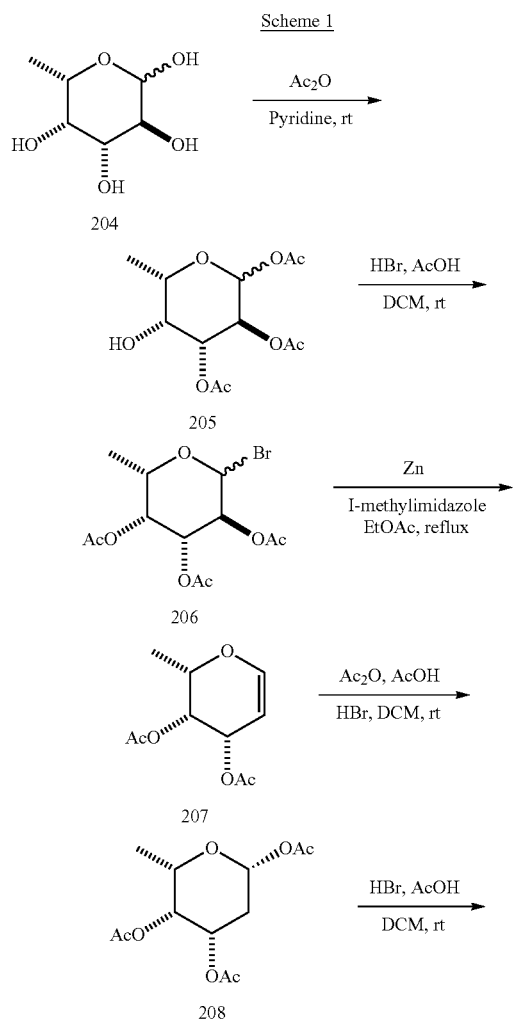

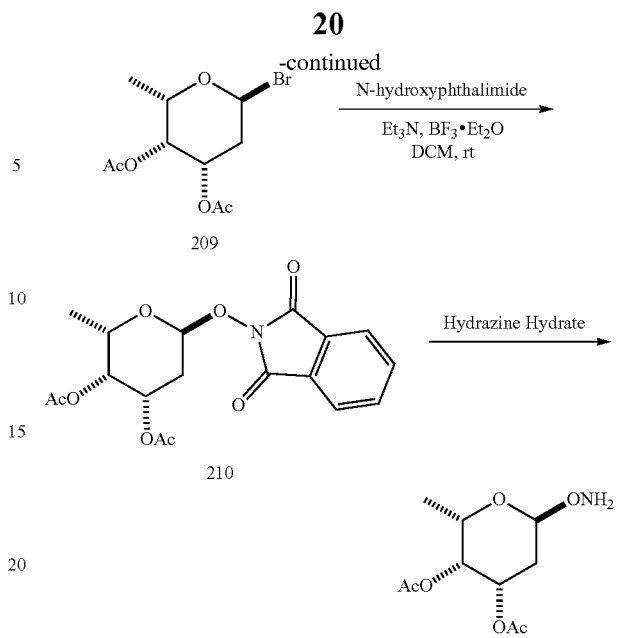

Scheme 1 illustrate preparation of compound 211.

1,2,3,4-Tetra-O-acetyl-L-fucose (205)

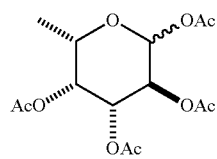
205

L-Fucose (204) (50 g, 0.3 mol) was dissolved in a solution of acetic anhydride (400 mL, 4.23 mol) and pyridine (800 mL, 9.9 mol). The reaction mixture was stirred at room temperature overnight, concentrated under reduced pressure, the residue diluted with EtOAc (2000 mL), washed with water (1000 mL), 10% aqueous citric acid (3×700 mL), water (1000 mL) and brine (1000 mL), dried over anhydrous $Na_2SO_4$, filtered and concentrated under reduced pressure. The residue was azeotroped with toluene (200 mL) and dried under high vacuum to afford the crude product 1,2,3,4-Tetra-O-acetyl-L-fucose (205) (100 g, quant.) which was used in the next step without any further purification.

(2S,3R,4R,5S)-4,5-bis(acetyloxy)-6-bromo-2-methyloxan-3-yl acetate (206)

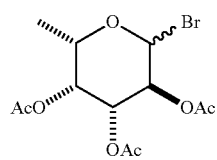
206

1,2,3,4-Tetra-O-acetyl-L-fucose (205) (101 g, 0.3 mol) was dissolved in anhydrous dichloromethane (500 mL) and cooled to 0° C. Then, HBr (33% in AcOH, 135 mL) was added, and the reaction mixture was allowed to warm to room temperature with stirring for 2 h. The reaction mixture was poured into an ice/water mixture and the organic layer was separated. The aqueous phase was extracted with CH₂Cl₂ (200 mL), washed with saturated NaHCO₃ (100 mL), brine (150 mL), dried over anhydrous Na₂SO₄, and concentrated under reduced pressure to yield (2S,3R,4R,5S)-4,5-bis(acetyloxy)-6-bromo-2-methyloxan-3-yl acetate, compound (206) (115 g, quant.) as a yellow oil. The crude material was used in the next step without further purification.

(2S,3R,4S)-4-(acetyloxy)-2-methyl-3,4-dihydro-2H-pyran-3-yl acetate (207)

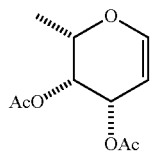

207

To a stirred solution of Zn (111 g, 1.7 mol) and 1-methylimidazole (25 mL, 0.31 mol) in anhydrous ethyl acetate (1200 mL) at reflux, was added a solution of (2S,3R,4R,5S)-4,5-bis(acetyloxy)-6-bromo-2-methyloxan-3-yl acetate (206) (100 g, 0.28 mol) in anhydrous ethyl acetate (200 mL) drop wise over 40 minutes. The reaction mixture was heated at reflux for 3 h until TLC analysis showed that the reaction was complete. The reaction mixture was cooled to room temperature and stirred for another 30 minutes and then filtered through a pad of celite. Concentration under reduced pressure afforded a crude product which was purified by silica gel flash chromatography (0-10% EtOAc in hexanes) to afford desired product (2S,3R,4S)-4-(acetyloxy)-2-methyl-3,4-dihydro-2H-pyran-3-yl acetate, compound (207) (38 g, 63% yield).

(2S,3R,4S)-4,6-bis(acetyloxy)-2-methyloxan-3-yl acetate (208)

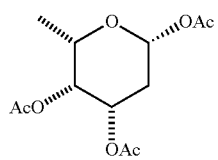

208

To a cold solution (ice/water bath) of (2S,3R,4S)-4-(acetyloxy)-2-methyl-3,4-dihydro-2H-pyran-3-yl acetate, compound (207) (75 g, 0.35 mol) in anhydrous dichloromethane (500 mL) was added acetic acid (190 mL, 3.3 mol) and acetic anhydride (290 mL, 3 mol). The reaction mixture was stirred for 15 minutes and 33% HBr solution in AcOH (19 mL) was added. The reaction mixture was stirred for an additional 30 minutes at which point the solution turned light yellow. TLC analysis showed complete consumption of starting material (lower spot, 25% EtOAc/hexanes). An ice/water mixture was added to quench the reaction. The organic layer was thoroughly washed with water (2×1 L) followed by cold saturated aqueous NaHCO₃ solution (1 L), water (1 L) and brine (1 L). The organic layer was dried over anhydrous Na₂SO₄ and concentrated in vacuo to provide a crude product which was purified by silica gel flash chromatography (0-20% EtOAc in hexanes) to afford desired product (2S,3R,4S)-4,6-bis(acetyloxy)-2-methyloxan-3-yl acetate, compound (208) as a white solid (83 g, 86.2% yield).

(2S,3R,4S,6S)-4-(acetyloxy)-6-bromo-2-methyloxan-3-yl acetate (209)

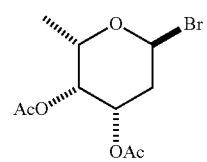

209

To a solution of (2S,3R,4S)-4,6-bis(acetyloxy)-2-methyloxan-3-yl acetate (208) (82 g, 0.3 mol) in anhydrous dichloromethane (700 mL) was added 33% HBr in AcOH (80 mL) at 0° C. The reaction mixture was stirred for 15 minutes, and then ice-cold water (300 mL) was added to quench the reaction. The aqueous phase was extracted with dichloromethane (3×700 mL) and the combined organic layers were washed with brine (2×500 mL), dried over anhydrous sodium sulfate and concentrated in vacuo to give (2S,3R,4S,6S)-4-(acetyloxy)-6-bromo-2-methyloxan-3-yl acetate, compound (209) as sticky oil. The crude material was taken forward into next step without any further purification as soon as possible.

(2S,3R,4S,6S)-4-(acetyloxy)-6-[(1,3-dioxo-2,3-dihydro-1H-isoindol-2-yl)oxy]-2-methyloxan-3-yl acetate (210)

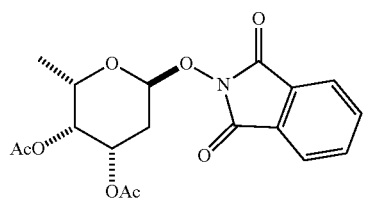

210

To a solution of crude (2S,3R,4S,6S)-4-(acetyloxy)-6-bromo-2-methyloxan-3-yl acetate (209) and N-hydroxyphthalimide (54 g, 0.33 mol) in anhydrous dichloromethane (600 mL) was added triethylamine (55 mL, 0.33 mol) followed by BF₃OEt₂ (92 mL, 0.75 mol) at 0° C. The reaction mixture was brought to room temperature and stirred for 1 h until it turned greenish gray in color. Cold saturated aqueous NaHCO₃ solution (500 mL) was added, and the organic layer separated. The aqueous layer was extracted with dichloromethane (3×500 mL) and the combined organic layers were dried over anhydrous sodium sulfate and concentrated under reduced pressure to obtain crude material. Silica gel flash chromatography (10%-60% EtOAc in hexanes) provided (2S,3R,4S,6S)-4-(acetyloxy)-6-[(1,3-dioxo-2,3-dihydro-1H-isoindol-2-yl)oxy]-2-methyloxan-3-yl acetate (210) as white foamy solid (75 g, 66% yield over two steps). LC/MS (Method B): RT=4.32 Min; m/z=377.1, found=378.2 [M+H]+. Total time=12 minutes. 1H NMR (500 MHz, CDCl3): δ 7.85 (ddd, J=5.5, 3.3, 0.6 Hz, 2H), 7.76 (ddd, J=5.9, 2.9, 0.8 Hz, 2H), 5.62-5.52 (m, 1H), 5.43 (ddd, J=12.5, 5.3, 3.0 Hz, 1H), 5.38-5.23 (m, 1H), 4.97 (td, J=6.7, 6.7, 5.6 Hz, 1H), 2.35-2.18 (m, 2H), 2.17 (s, 3H), 2.03 (d, J=0.6 Hz, 3H), 1.14 (dd, J=6.5, 0.6 Hz, 3H).

Example 1: (2S,3R,4S,6S)-4-(acetyloxy)-6-(aminooxy)-2-methyloxan-3-yl acetate (211)

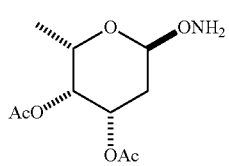

211

A solution of (2S,3R,4S,6S)-4-(acetyloxy)-6-[(1,3-dioxo-2,3-dihydro-1H-isoindol-2-yl)oxy]-2-methyloxan-3-yl acetate (210) (25 g, 0.066 mol) in methanol (500 mL) was cooled to 0° C. under an ice/water bath. Hydrazine hydrate (5.5 mL, 0.066 mol) was added slowly and the resulting reaction mixture was stirred for additional 30 minutes at 0° C. The precipitate was filtered, and the filtrate was diluted with dichloromethane (500 mL), washed with cold aqueous NaHCO3 (2×350 mL), water (350 mL) and brine (350 mL). The organic layer was dried over anhydrous Na2SO4 and concentrated under reduced pressure to afford crude (2S,3R,4S,6S)-4-(acetyloxy)-6-(aminooxy)-2-methyloxan-3-yl acetate, compound (211) (12 g, 78% yield) as off white foamy solid. LC/MS (Method A): RT=1.22 Minutes; m/z=247.2, found=248.3 [M+H]+. Total time=6 minutes.

Scheme 2 illustrate preparation of compound 217.

Scheme 2

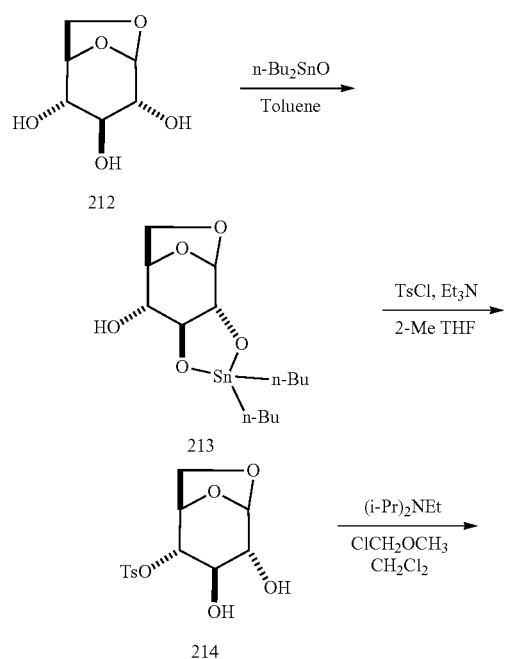

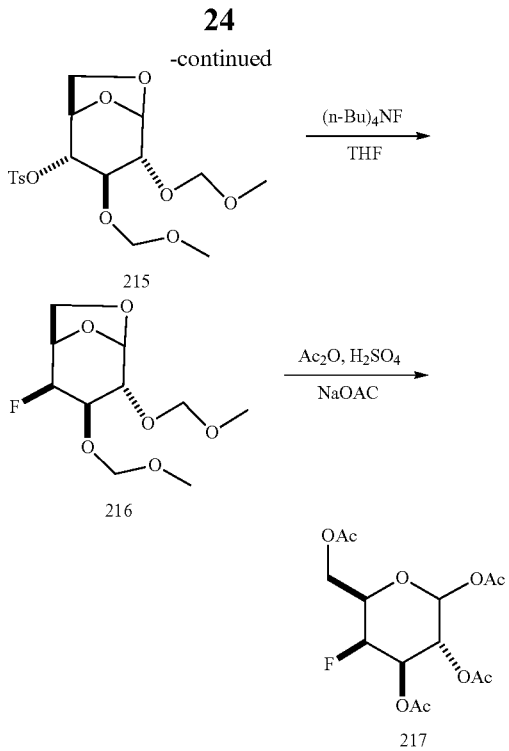

(1R,2R,6S,7R,8R)-4,4-dibutyl-3,5,10,11-tetraoxa-4-stannatricyclo[6.2.1.02,6]undecan-7-ol (213)

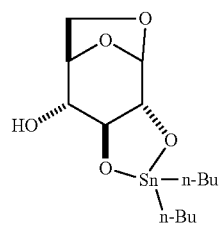

213

A mixture of 1,6-anhydro-β-D-glucose (212) (5.00 g, 30.8 mmol, 1.00 eq) and dibutyltin(IV) oxide (7.68 g, 30.8 mmol, 1.00 eq) in toluene (150 mL) was refluxed for 12 h in an apparatus equipped for the azeotropic removal of water (see Grindley et al., Carbohydrate Res. 1988, 172, 311). The cooled mixture was evaporated under reduced pressure to give the crude stannylene derivative (213) as a white semi-solid, which was used without purification.

1,6-anhydro-4-O-p-tolylsulfonyl-β-D-glucopyranose (214)

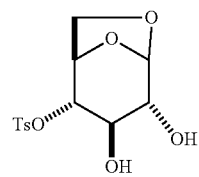

214

To a solution of (1R,2R,6S,7R,8R)-4,4-dibutyl-3,5,10,11-tetraoxa-4-stannatricyclo[6.2.1.02,6]undecan-7-ol (213) (12.54 g, 31.9 mmol, 1.00 eq) in tetrahydrofuran (300 mL) was added triethylamine (4.9 mL, 35.1 mmol, 1.10 eq) and powdered 4A molecular sieves (3 g). p-Toluenesulfonyl chloride (6.69 g, 35.1 mmol, 1.10 eq) was added and the mixture was stirred vigorously for 2 days and then filtered through Celite. The filtrate was evaporated, and the residue was diluted with dichloromethane (150 mL). The organic solution was washed with water (2×50 mL), dried (sodium sulfate) and evaporated. The crude material was purified by column chromatography on silica gel using 7:3 dichloromethane: 2-methyltetrahydrofuran as the eluant. The first component to elute was 1,6-anhydro-2,4-di-O-p-tolylsulfonyl-β-D-glucopyranose which separated easily. The second component was the desired product (214) (~8 g colorless oil) which was contaminated with the other regioisomer 1,6-anhydro-2-O-p-tolylsulfonyl-o-D-glucopyranose which was difficult to separate. The mixture was recrystallized from a mixture of acetone, ether, and petroleum ether (b.p. 30-60° C.) to give the desired product (214) as white needles. A second recrystallisation gave the pure product (2.2 g, 22%) as a single regioisomer. $^1$H NMR (400 MHz, CDCl$_3$): δ 7.83 (d, J=8.3 Hz, 2H), 7.38 (d, J=8.1 Hz, 2H), 5.48 (s, 1H), 4.65 (d, J=5.4 Hz, 1H), 4.42 (s, 1H), 4.13 (d, J=8.1 Hz, 1H), 3.79-3.71 (m, 2H), 3.49 (dd, J=0.9, 11.3 Hz, 1H), 2.50 (d, J=7.5 Hz, 1H), 2.47 (s, 3H), 2.32 (d, J=11.4 Hz, 1H).

1,6-Anhydro-2,3-bis(O-methoxymethyl)-4-O-(4-toluenesulfonyl)-β-D-glucopyranose (215)

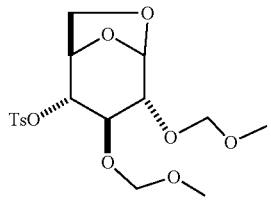

215

To a stirred solution of [(1R,2S,3R,4R,5R)-3,4-dihydroxy-6,8-dioxabicyclo[3.2.1]octan-2-yl] 4-methylbenzenesulfonate (214) (2.20 g, 6.95 mmol, 1.00 eq) in dichloromethane (50 mL) were added N,N-diisopropylethylamine (13 mL, 76.5 mmol, 11.0 eq) and chloromethyl methyl ether (5.3 mL, 69.5 mmol, 10.0 eq). The mixture was stirred at 40° C. for 4 h resulting in a brown solution. The solution was cooled and then quenched with water (50 mL). The mixture was extracted with dichloromethane (2×50 mL) and the combined organic phases were washed with brine (100 mL). The organic solution was dried over sodium sulfate, filtered, and concentrated under reduced pressure. The crude residue was purified by flash column chromatography (silica gel 40 g, ethyl acetate/hexanes, 5-50%) to give [(1R,2R,3R,4R,5R)-3,4-bis(methoxymethoxy)-6,8-dioxabicyclo[3.2.1]octan-2-yl] 4-methylbenzenesulfonate (215) (2.10 g, 5.19 mmol, 75%) as a colorless oil. Rf=0.5 (silica, ethyl acetate/cyclohexane 1:1). $^1$H NMR (400 MHz, CDCl$_3$): δ 7.84 (d, J=8.3 Hz, 2H), 7.36 (d, J=8.1 Hz, 2H), 5.46 (s, 1H), 4.68-4.63 (m, 2H), 4.59 (s, 2H), 4.58-4.53 (m, 1H), 4.44 (s, 1H), 4.04 (d, J=7.7 Hz, 1H), 3.86-3.84 (m, 1H), 3.71 (dd, J=6.0, 7.5 Hz, 1H), 3.52-3.50 (m, 1H), 3.37 (s, 3H), 3.32 (s, 3H), 2.45 (s, 3H).

1,6-Anhydro-4-deoxy-4-fluoro-2,3-bis(O-methoxymethyl)-β-D-galactopyranose) (216)

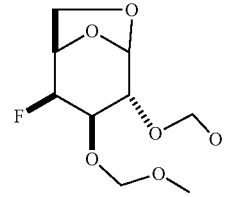

216

[(1R,2R,3R,4R,5R)-3,4-bis(methoxymethoxy)-6,8-dioxabicyclo[3.2.1]octan-2-yl] 4-methylbenzenesulfonate (215) (2.10 g, 5.19 mmol, 1.00 eq) was stirred in tetrabutylammonium fluoride (1M in THF, 55 mL, 10 equiv.) under reflux for 5 days. The black mixture was cooled and evaporated. The residue was diluted with water (100 mL) and the mixture was extracted with ethyl acetate (3×50 mL). The combined organic phases were washed with brine (100 mL), dried over sodium sulfate, filtered, and concentrated under reduced pressure. The crude material was purified by flash column chromatography (silica gel, ethyl acetate/cyclohexane, 0-30%) to give (1R,2S,3R,4R,5R)-2-fluoro-3,4-bis(methoxymethoxy)-6,8-dioxabicyclo[3.2.1]octane (216) as a pale-yellow oil (470 mg, 25% yield, 70% purity). This inseparable mixture containing the desired fluoro product and an unknown other product was used for the next step without further purification. Rf=0.51 (silica, ethyl acetate/cyclohexane 2:3). $^1$H NMR (400 MHz, CDCl$_3$) was consistent with the product (215) as the major component (~70% pure).

Example 2: 1,2,3,6-Tetra-O-acetyl-4-deoxy-4-fluoro-α/β-D-galactopyranose (217)

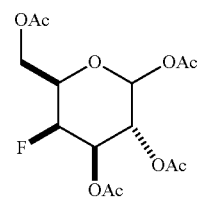 [SMILES: CC(=O)OC[C@H]1OC(OC(C)=O)[C@H](OC(C)=O)[C@@H](OC(C)=O)[C@H]1F]

217

To a stirred solution of the mixture containing compound (1R,2S,3R,4R,5R)-2-fluoro-3,4-bis(methoxymethoxy)-6,8-dioxabicyclo[3.2.1]octane (216) (470 mg, 1.86 mmol, 1.00 eq) (70% pure) in acetic anhydride (5.3 mL, 55.9 mmol, 30.0 eq) at 0° C. was added sulfuric acid (0.99 mL, 18.6 mmol, 10.0 eq) dropwise. The mixture was stirred at room temperature for 72 h. The mixture was then cooled to 0° C., and sodium acetate (3.06 g, 37.3 mmol, 20.0 eq) was added, stirred for an additional 20 minutes and then quenched with water (20 mL). The mixture was extracted with dichloromethane (3×15 mL). The combined organic phases were successively washed with water (3×30 mL) and brine (30 mL), dried over sodium sulfate, filtered, and concentrated under reduced pressure. The crude residue was purified by flash column chromatography (silica gel, 12 g 15 m, ethyl acetate in cyclohexane, 1-40%) to give an anomeric mixture (α/β=4:1) of product [(2R,3S,4R,5R)-4,5,6-triacetoxy-3- fluoro-tetrahydropyran-2-yl]methyl acetate (217) (360 mg, 0.925 mmol, 50%) as a colorless oil (360 mg, 90% pure, ~50% yield). Rf=0.4 (silica, AcOEt/hexanes, 1:1). $^1$H NMR (400 MHz, CDCl$_3$): δ 6.39 (d, J=3.5 Hz, 1H), 5.43-5.39 (m, 1H), 5.32-5.21 (m, 1H), 4.97 (dd, J=2.7, 50.2 Hz, 1H), 4.32-4.16 (m, 3H), 2.16 (s, 3H), 2.14 (s, 3H), 2.09 (s, 3H), 2.03 (s, 3H).

Scheme 3 illustrate preparation of compounds 222 and 223.

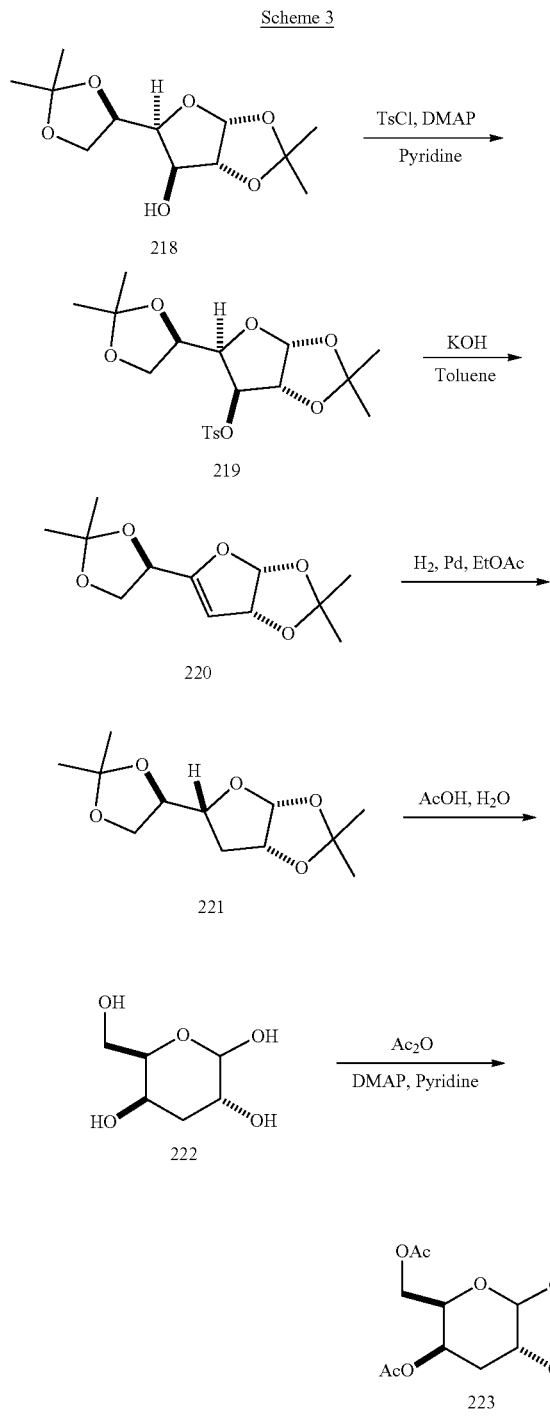

Scheme 3

[(3aR,5R,6S,6aR)-5-[(4R)-2,2-dimethyl-1,3-dioxolan-4-yl]2,2-dimethyl-3a,5,6,6a-tetrahydrofuro[2,3-d][1,3]dioxol-6-yl] 4-methylbenzenesulfonate (219)

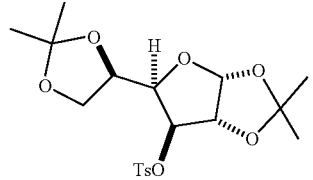

219

1,2:5,6-Di-O-isopropylidene-alpha-D-glucofuranose (218) (5000 mg, 19.2 mmol, 1.00 eq) was dissolved in pyridine (30 mL) and 4-(dimethylamino)pyridine (235 mg, 1.92 mmol, 0.1000 eq) was added followed by p-toluenesulfonyl chloride (7.32 g, 38.4 mmol, 2.00 eq). The pale-yellow reaction mixture was stirred at room temperature overnight. TLC analysis (EtOAc/cyclohexane 1:2) showed ~1:1 starting material to product. Additional 4-(dimethylamino)pyridine (235 mg, 1.92 mmol, 0.1000 eq) was added and the mixture was stirred for 72 h and the solvent was removed in vacuo. The residue was dissolved in EtOAc and the solution washed with water (3× to remove residual pyridine), brine, dried and evaporated. The crude material was purified by silica chromatography (silica 120 g, EtOAc in cyclohexane 0-20%) which removed unreacted TsCl and the product was eluted. Product fractions were combined and evaporated to give the title compound as a white crystalline substance (219) (7 g, 88%). $^1$H NMR (400 MHz, CDCl$_3$): δ 7.84 (d, J=8.3 Hz, 2H), 7.34 (d, J=8.1 Hz, 2H), 5.92 (d, J=3.7 Hz, 1H), 4.84 (d, J=3.8 Hz, 1H), 4.79 (d, J=2.4 Hz, 1H), 4.06-3.89 (m, 4H), 2.46 (s, 3H), 1.48 (s, 3H), 1.31 (s, 3H), 1.20 (s, 3H), 1.15 (s, 3H).

(3aR,6aR)-5-[(4R)-2,2-dimethyl-1,3-dioxolan-4-yl]-2,2-dimethyl-3a, 6a-dihydrofuro[2,3-d][1,3]dioxole (220)

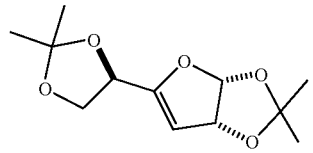

220

[(3aR,5R,6S,6aR)-5-[(4R)-2,2-dimethyl-1,3-dioxolan-4-yl]-2,2-dimethyl-3a,5,6,6a-tetrahydrofuro[2,3-d][1,3]dioxol-6-yl] 4-methylbenzenesulfonate (219) (7.00 g, 16.9 mmol, 1.00 eq) was dissolved in toluene (250 mL) and potassium hydroxide (2.94 g, 52.4 mmol, 3.10 eq) (crushed to a fine powder) was added. The reaction was heated under reflux for 5 h. TLC (25% EtOAc in cyclohexane) showed the product as the most non-polar spot with starting material just below and a more polar side product (unidentified). Heating was continued until all starting material was consumed. The reaction mixture was cooled to room temperature and water (250 mL) was added. The layers were separated, and the organic layer was washed with brine, dried (MgSO$_4$) and the solvent removed in vacuo to give a pale-yellow oil, which was purified by silica chromatography (80 g, eluting with EtOAc/cyclohexane 0-30%) to give the title compound (220) as a clear oil (2.9 g, 70%) which crystallized to give a white solid on standing. ¹H NMR (400 MHz, CDCl₃): 6.08 (d, J=5.2 Hz, 1H), 5.32-5.29 (m, 1H), 5.25-5.24 (m, 1H), 4.60-4.57 (m, 1H), 4.15 (dd, J=6.8, 8.4 Hz, 1H), 3.97 (dd, J=5.7, 8.4 Hz, 1H), 1.47 (s, 6H), 1.45 (s, 3H), 1.39 (s, 3H).

(3aR,5R,6aR)-5-[(4R)-2,2-dimethyl-1,3-dioxolan-4-yl]-2,2-dimethyl-3a,5,6,6a-tetrahydrofuro[2,3-d][1,3]dioxole (221)

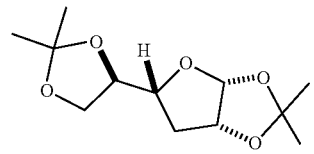

221

A solution of (3aR,6aR)-5-[(4R)-2,2-dimethyl-1,3-dioxolan-4-yl]-2,2-dimethyl-3a,6a-dihydrofuro[2,3-d][1,3]dioxole (220) (2.80 g, 11.6 mmol, 1.00 eq) in ethyl acetate (100 mL) was placed under argon. Palladium (10%, 1230 mg, 1.16 mmol, 0.100 eq) was moistened with ethyl acetate under CO₂ and added to the above solution. The mixture was evacuated and purged with argon (3×) and then stirred under a balloon of hydrogen overnight. TLC (25% EtOAc in cyclohexane) indicated all starting material had reacted and one major product (more polar than starting material) and a by-product were formed. The crude mixture was purged with argon and evacuated (3×) and the catalyst removed by filtration through Celite. The filtrate was concentrated, and the crude material was purified by column chromatography using 0-30% ethyl acetate in cyclohexane as eluant. Product fractions (located by Hanessian staining) were combined and evaporated to give the title compound (221) as a white crystalline solid (1.51 g, 53%). ¹H NMR (400 MHz, CDCl₃): 5.80 (d, J=3.8 Hz, 1H), 4.75-4.71 (m, 1H), 4.47-4.41 (m, 1H), 4.14-4.08 (m, 1H), 4.05 (dd, J=6.6, 8.2 Hz, 1H), 3.61 (dd, J=6.9, 8.2 Hz, 1H), 2.21 (ddd, J=6.1, 8.3, 14.3 Hz, 1H), 1.82 (ddd, J=1.2, 3.9, 14.3 Hz, 1H), 1.57 (s, 3H), 1.45-1.44 (m, 3H), 1.37 (s, 3H), 1.33 (s, 3H).

Example 3: (3R,5R,6R)-6-(hydroxymethyl)tetrahydropyran-2,3,5-triol (221)

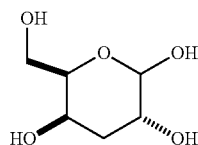

222

A mixture of acetic acid (20.195 mL) and water (20.20 mL) was added to (3aR,5R,6aR)-5-[(4R)-2,2-dimethyl-1,3-dioxolan-4-yl]-2,2-dimethyl-3a,5,6,6a-tetrahydrofuro[2,3-d][1,3]dioxole (221) (1.48 g, 6.06 mmol, 1.00 eq) and the resulting solution heated at 70° C. for 12 h. The solvent was evaporated, and the residue dried in vacuo to give 1.2 g of crude material as a viscous oil. ¹H NMR (400 MHz, CD₃OD, 263384) was consistent with a mixture of 3-4 isomeric products. No attempt to purify further was made due to the polarity of the compounds.

Example 5: [(2R,3R,5R)-3,5,6-triacetoxytetrahydropyran-2-yl]methyl acetate (223)

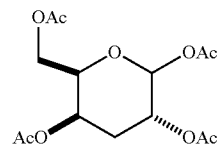

223

(3R,5R,6R)-6-(hydroxymethyl)tetrahydropyran-2,3,5-triol (222) (90% pure, 1.20 g, 6.58 mmol, 1.00 eq) was suspended in pyridine (21.93 mL) and acetic anhydride (3.7 mL, 39.5 mmol, 6.00 eq) and 4-(dimethylamino)pyridine (80 mg, 0.658 mmol, 0.100 eq) were added. Addition of DMAP led to a slight exotherm which persisted for ~20 minutes. The pale-yellow solution was stirred for 1 h. TLC (ethyl acetate-cyclohexane 1:1) showed one major product. The solution was concentrated in vacuo, the residue dissolved in ethyl acetate and washed with water (3×), dried (brine, sodium sulfate) and evaporated. The residue was purified on silica using 0-50% ethyl acetate in cyclohexane to give the product (0.62 g) as a clear oil. ¹H NMR was consistent with a mixture of 3-4 isomeric products. The oil was re-purified on silica (40 g, 15 µm) using 0-50% TBDME in cyclohexane to give: (a) (223) (220 mg white solid, 10%): ¹H NMR (400 MHz, CDCl₃) consistent with desired product (axial acetate, pyran) d, 6.29 (d, J=3.1 Hz, 1H), 5.24-5.17 (m, 2H), 4.20-4.03 (m, 3H), 2.16 (s, 3H), 2.13 (s, 3H), 2.06 (s, 3H), 2.02 (s, 3H), 2.18-2.04 (m, 2H, partially hidden under acetates); and b) (223) (enriched sample was further purified by crystallization from ether) 200 mg 10% consistent with product (equatorial acetate, pyran) d, 5.71 (d, J=8.3 Hz, 1H), 5.14-5.02 (m, 2H), 4.21-4.00 (m, 3H), 2.45 (ddd, J=3.5, 5.1, 14.2 Hz, 1H), 2.13 (s, 6H), 2.06 (s, 3H), 2.05 (s, 3H), 1.80 (ddd, J=3.1, 11.3, 14.3 Hz, 1H).

Scheme 4 illustrate preparation of compounds 227, 228 and 229.

Scheme 4

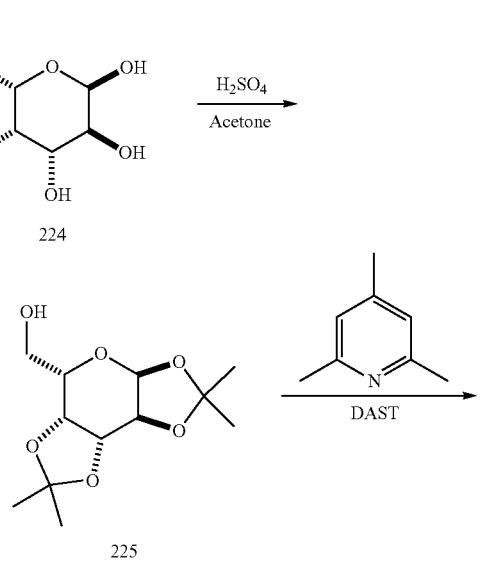

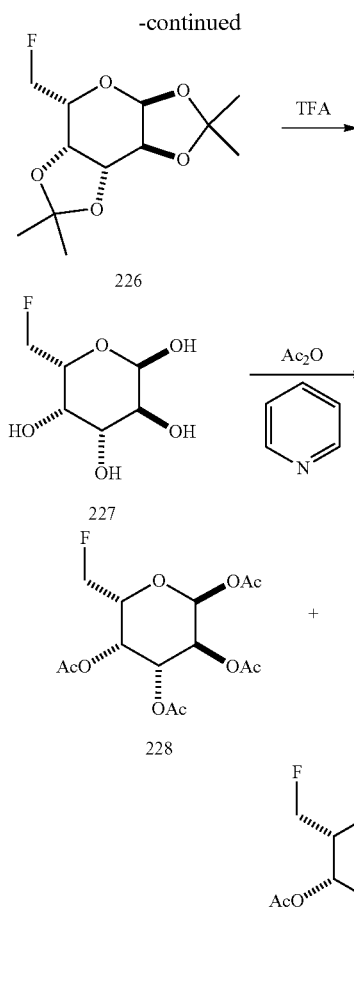

228

229

[(1R,2S,6S,8S,9R)-4,4,11,11-tetramethyl-3,5,7,10, 12-pentaoxatricyclo[7.3.0.02,6]dodecan-8-yl]methanol (225)

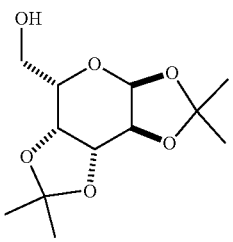

225

A mixture of (2R,3S,4R,5S,6S)-6-(hydroxymethyl)tetrahydropyran-2,3,4,5-tetrol (5.00 g, 27.8 mmol, 1.00 eq) (L-galactose) (224) in acetone (185 mL) was treated with conc. sulfuric acid (5.5 mL, 0.103 mol, 3.72 eq) at 0° C. The reaction mixture was stirred at room temperature for 3 h. At this time the starting material had dissolved, and the mixture had clarified to give a pale-yellow solution. TLC (ethyl acetate/cyclohexane 1:3) showed mostly product but also some baseline material. TLC (20% methanol in dichloromethane) showed no starting material but a small amount of a more polar product (possibly the mono-acetonide). The solution was stirred overnight. The pale brown solution was neutralized by the addition of water (5 mL) and solid sodium carbonate (~80 g). The mixture was stirred for ~30 minutes and the precipitate was removed by filtration through a pad of Celite. The filtrates were combined and concentrated under reduced pressure to provide a residue which was purified on silica (80 g) using 5-50% ethyl acetate in cyclohexane as eluant. This gave the product (225) as a colorless oil (6.26 g, 81%). $^1$H NMR (400 MHz, CDCl$_3$): d, 5.57 (d, J=5.1 Hz, 1H), 4.62 (dd, J=2.4, 7.9 Hz, 1H), 4.34 (ddd, J=2.5, 2.5, 2.5 Hz, 1H), 4.28 (dd, J=1.5, 7.9 Hz, 1H), 3.91-3.82 (m, 2H), 3.79-3.71 (m, 1H), 1.53 (s, 3H), 1.47 (s, 3H), 1.34 (s, 6H)).

(1R,2S,6S,8R,9S)-8-(fluoromethyl)-4,4,11,11-tetramethyl-3,5,7,10,12-pentaoxatricyclo[7.3.0.02,6] dodecane (226)

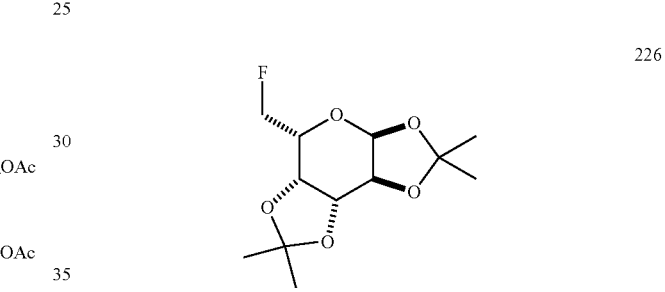

226

A solution of 1,2,3,4-di-O-isopropylidene-L-galactopyranose [(1R,2S,6S,8S,9R)-4,4,11,11-tetramethyl-3,5,7,10,12-pentaoxatricyclo[7.3.0.02,6]dodecan-8-yl]methanol (225) (1.00 g, 3.84 mmol, 1.00 eq) in dichloromethane (6 mL) was treated with 2,4,6-trimethylpyridine (1.0 mL, 7.68 mmol, 2.00 eq) and the solution was cooled to 0° C. (Diethylamino) sulfur trifluoride (1.0 mL, 7.68 mmol, 2.00 eq) was added dropwise over 5 minutes and the mixture was stirred at 0° C. for 1 h and at room temperature for 2 h. TLC (20% ethyl acetate in cyclohexane) confirmed complete consumption of the starting material and the solution was stirred overnight. TLC (ethyl acetate: cyclohexane 1:1) showed the disappearance of starting material and the production of a less polar compound. The reaction mixture was diluted with dichloromethane (20 mL), washed with NaHCO$_3$, 1 M HCl, brine (25 mL), dried over sodium sulfate and concentrated. The residue was purified by silica gel chromatography (eluting with 0-20% ethyl acetate in cyclohexane) to give (1R,2S, 6S,8R,9S)-8-(fluoromethyl)-4,4,11,11-tetramethyl-3,5,7,10, 12-pentaoxatricyclo[7.3.0.02,6]dodecane (226) (288 mg, 1.10 mmol, 29%) as a colorless syrup. $^1$H NMR (400 MHz, CDCl$_3$): d, 5.55 (d, J=5.0 Hz, 1H), 4.66-4.57 (m, 2H), 4.55-4.45 (m, 1H), 4.35 (dd, J=2.5, 5.0 Hz, 1H), 4.27 (dd, J=2.0, 7.9 Hz, 1H), 4.12-4.05 (m, 1H), 1.55 (s, 3H), 1.46 (s, 3H), 1.34 (s, 6H).

Example 6: (3S,4R,5S,6R)-6-(fluoromethyl)tetrahydropyran-2,3,4,5-tetrol (227)

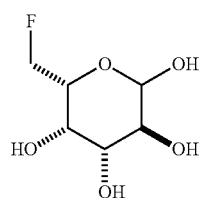

227

(1R,2S,6S,8R,9S)-8-(fluoromethyl)-4,4,11,11-tetramethyl-3,5,7,10,12-pentaoxatricyclo[7.3.0.02,6]dodecane (368 mg, 1.40 mmol, 1.00 eq) (226) was dissolved in 90% TFA (4 mL) and the mixture was stirred at room temperature for 15 minutes. The solvent was removed in vacuo and co-evaporated with toluene twice and dried in vacuo. $^1$H NMR (400 MHz, MeOD-$d_4$) was consistent with the product (227) (255 mg, 1.40 mmol, 100%) as a mixture of anomers. This polar material was taken to the next step without further purification.

Example 7: [(2R,3S,4R,5S,6S)-4,5,6-triacetoxy-2-(fluoromethyl)tetrahydropyran-3-yl]acetate (228) and [(2R,3S,4R,5S,6R)-4,5,6-triacetoxy-2-(fluoromethyl)tetrahydropyran-3-yl] acetate (229)

228

229

Crude (3S,4R,5S,6R)-6-(fluoromethyl)tetrahydropyran-2,3,4,5-tetrol (227) (255 mg, 1.40 mmol, 1.00 eq) was dissolved in pyridine (5 mL) and cooled in ice water under nitrogen. Acetic anhydride (1.3 mL, 14.0 mmol, 10.0 eq) was added dropwise and the resulting mixture was stirred for 12 h at room temperature. The mixture was evaporated to dryness and azeotroped with toluene (2×). The crude material was purified on silica (12 g, 15 µm) using 0-30% ethyl acetate in cyclohexane to give a) 1$^{st}$ eluting product the α-anomer [(2R,3S,4R,5S,6S)-4,5,6-triacetoxy-2-(fluoromethyl)tetrahydropyran-3-yl] acetate (228) (64 mg, 0.183 mmol, 13%): $^1$H NMR (400 MHz, CDCl$_3$): δ 6.41 (s, 1H), 5.58-5.55 (m, 1H), 5.37-5.34 (m, 2H), 4.54-4.29 (m, 3H), 2.17 (s, 3H), 2.16 (s, 3H), 2.03 (s, 3H), 2.01 (s, 3H); and b) 2$^{nd}$ eluting product the β-anomer [(2R,3S,4R,5S,6R)-4,5,6-triacetoxy-2-(fluoromethyl)tetrahydropyran-3-yl] acetate (229) (189 mg, 0.540 mmol, 39%): $^1$H NMR (400 MHz, CDCl$_3$): d, 5.73 (d, J=8.3 Hz, 1H), 5.50 (d, J=3.3 Hz, 1H), 5.36 (dd, J=8.3, 10.4 Hz, 1H), 5.10 (dd, J=3.4, 10.4 Hz, 1H), 4.58-4.33 (m, 2H), 4.16-4.03 (m, 1H), 2.18 (s, 3H), 2.13 (s, 3H), 2.05 (s, 3H), 2.01 (s, 3H).

Scheme 5 illustrate preparation of compound 230.

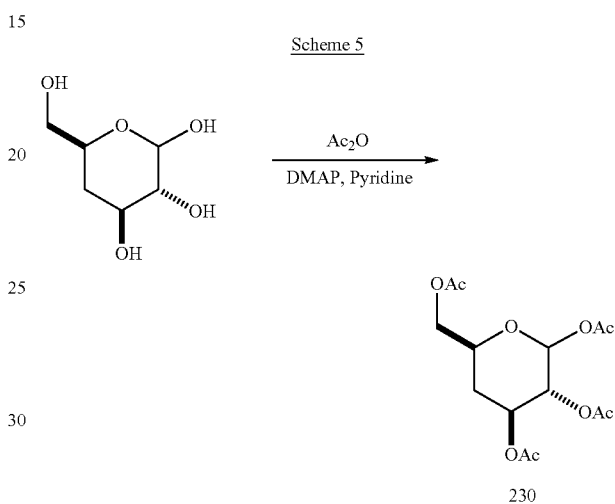

Scheme 5

230

Example 8: (2R,3R,4S,6S)-6-(acetoxymethyl)tetrahydro-2H-pyran-2,3,4-triyl triacetate (230)

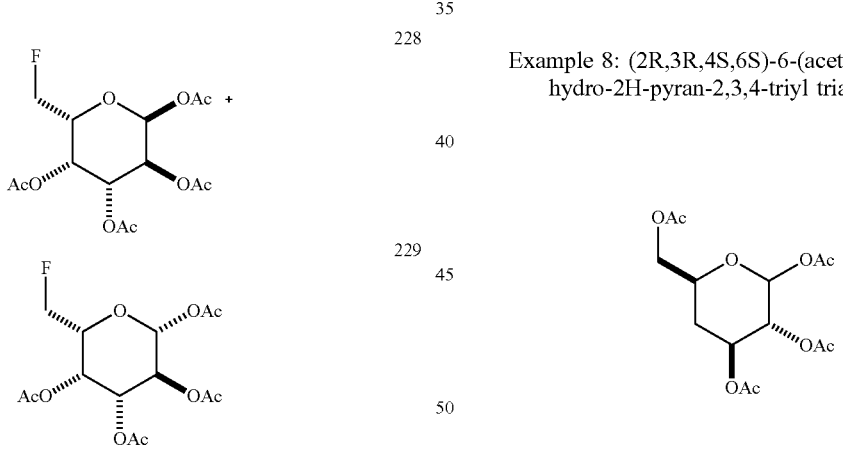

230

To a solution of (3R,4S,6S)-6-(hydroxymethyl)tetrahydropyran-2,3,4-triol (500 mg, 3.05 mmol, 1.00 eq) and 4-(dimethylamino)pyridine (37 mg, 0.305 mmol, 0.100 eq) in pyridine (10 mL) at 0° C. was added acetic anhydride (4.3 mL, 45.7 mmol, 15.0 eq) over a period of ten minutes and the reaction mixture was stirred at 0° C. for 2.5 h. The reaction mixture was concentrated to a minimum volume and the remaining pyridine co-evaporated with toluene. The oily residue was re-dissolved in toluene and washed with 1M HCl, water and brine. The organic phase was dried (Na$_2$SO$_4$), filtered and concentrated to give the title compound (230) (993 mg, 98%). $^1$H NMR (300 MHz, CDCl$_3$): d, 5.69-5.65 (m, 1H), 5.09-4.99 (m, 2H), 4.19-4.15 (m, 2H), 3.96-3.87 (m, 1H), 2.23-2.16 (m, 1H), 2.12 (s, 3H), 2.10 (s, 3H), 2.06 (s, 6H), 1.73-1.59 (m, 1H).

Scheme 6 illustrate preparation of compound 236.

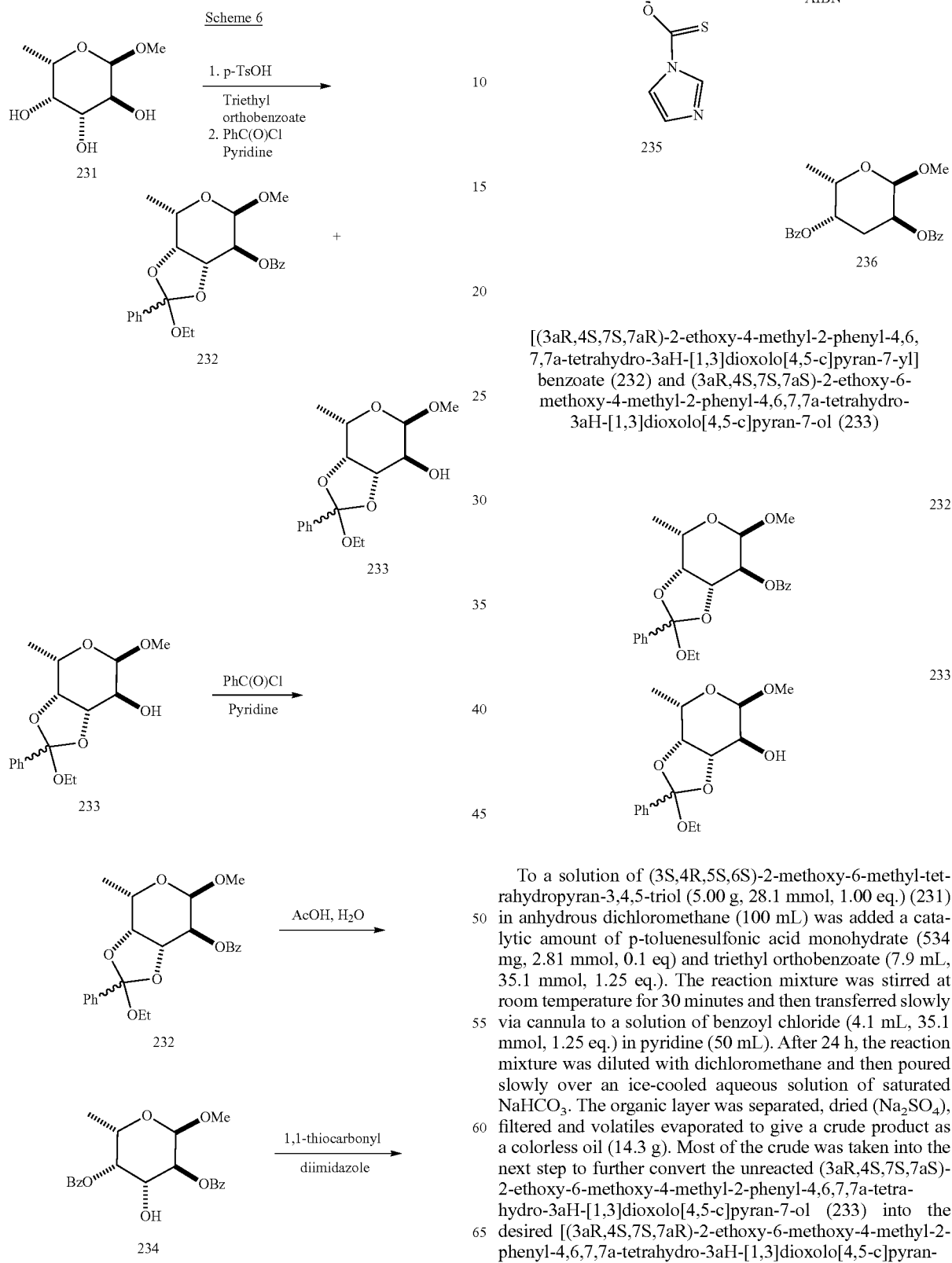

[(3aR,4S,7S,7aR)-2-ethoxy-4-methyl-2-phenyl-4,6,7,7a-tetrahydro-3aH-[1,3]dioxolo[4,5-c]pyran-7-yl] benzoate (232) and (3aR,4S,7S,7aS)-2-ethoxy-6-methoxy-4-methyl-2-phenyl-4,6,7,7a-tetrahydro-3aH-[1,3]dioxolo[4,5-c]pyran-7-ol (233)

To a solution of (3S,4R,5S,6S)-2-methoxy-6-methyl-tetrahydropyran-3,4,5-triol (5.00 g, 28.1 mmol, 1.00 eq.) (231) in anhydrous dichloromethane (100 mL) was added a catalytic amount of p-toluenesulfonic acid monohydrate (534 mg, 2.81 mmol, 0.1 eq) and triethyl orthobenzoate (7.9 mL, 35.1 mmol, 1.25 eq.). The reaction mixture was stirred at room temperature for 30 minutes and then transferred slowly via cannula to a solution of benzoyl chloride (4.1 mL, 35.1 mmol, 1.25 eq.) in pyridine (50 mL). After 24 h, the reaction mixture was diluted with dichloromethane and then poured slowly over an ice-cooled aqueous solution of saturated NaHCO₃. The organic layer was separated, dried (Na₂SO₄), filtered and volatiles evaporated to give a crude product as a colorless oil (14.3 g). Most of the crude was taken into the next step to further convert the unreacted (3aR,4S,7S,7aS)-2-ethoxy-6-methoxy-4-methyl-2-phenyl-4,6,7,7a-tetrahydro-3aH-[1,3]dioxolo[4,5-c]pyran-7-ol (233) into the desired [(3aR,4S,7S,7aR)-2-ethoxy-6-methoxy-4-methyl-2-phenyl-4,6,7,7a-tetrahydro-3aH-[1,3]dioxolo[4,5-c]pyran-7-yl] benzoate (232). For characterization purposes, a small amount of the crude product (290 mg) was taken for purification by flash chromatography, 4 g silica cartridge eluted with cyclohexane: ethyl acetate from 1-100%) to give two separated compounds: epimeric mixture of [(3aR,4S,7S,7aR)-2-ethoxy-6-methoxy-4-methyl-2-phenyl-4,6,7,7a-tetrahydro-3aH-[1,3]diox ol[4,5-c]pyran-7-yl] benzoate (56 mg) (232) as a colorless oil, and epimeric mixture of (3aR,4S,7S,7aS)-2-ethoxy-6-methoxy-4-methyl-1-phenyl-4,6,7,7a-tetrahydro-3aH-[1,3]dioxolo[4,5-c]pyran-7-ol (109 mg) (233) as a colorless oil.

[(3a,4S,7S,7aR)-2-ethoxy-6-methoxy-4-methyl-2-phenyl-4,6,7,7a-tetrahydro-3aH-[1,3]dioxolo[4,5-c]pyran-7-yl] benzoate (232)

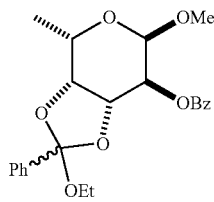

232

To a solution of crude (3aR,4S,7S,7aS)-2-ethoxy-6-methoxy-4-methyl-2-phenyl-4,6,7,7a-tetrahydro-3aH-[1,3]dioxolo[4,5-c]pyran-7-ol (12.56 g, 40.5 mmol, 1.00 eq.) (233) in pyridine (36 mL) at 0° C. was added benzoyl chloride (5.2 mL, 44.5 mmol, 1.10 eq). The reaction mixture was allowed to stir overnight at room temperature, concentrated and the residue partitioned between ethyl acetate and aqueous saturated NaHCO$_3$. The organic layer was separated and washed with water, dried (Na$_2$SO$_4$), filtered and the volatiles evaporated to give a crude product that was purified by flash chromatography, (110 g silica cartridge eluted with cyclohexane: ethyl acetate 0-30%) to give the title compound (232) (11.70 g, 70%) as a colorless oil.

(2S,3S,4R,5S)-5-benzoyloxy-4-hydroxy-6-methoxy-2-methyl-tetrahydropyran-3-yl] benzoate (234)

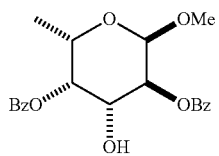

234

[(3aR,4S,7S,7aR)-2-ethoxy-6-methoxy-4-methyl-2-phenyl-4,6,7,7a-tetrahydro-3aH-[1,3]dioxolo[4,5-c]pyran-7-yl] benzoate (232) (11.77 g, 28.4 mmol, 1.00 eq.) was treated with acetic acid (56 mL) and water (14.00 mL) and the reaction mixture was stirred overnight at room temperature. The reaction mixture was concentrated, and the residue dissolved in ethyl acetate and poured into aqueous saturated NaHCO$_3$. The organic phase was separated and dried (Na$_2$SO$_4$), filtered and the volatiles evaporated to give a crude product (12.5 g). Recrystallization from ethyl acetate/dichloromethane, gave the title compound (234) (3.3 g, 30%) as a white solid. The mother liquors were further recrystallized from ethyl acetate: dichloromethane to give a second crop of the desired product (234) (2.46 g, 22%) as a white solid. The second mother liquors were concentrated to give an oily product (4.6 g) purified by flash chromatography, (80 silica cartridge eluted with cyclohexane: ethyl acetate (2-35%)) to give after evaporation more of the title compound (234) (1 g, 9%) as a white solid. $^1$H NMR (300 MHz, CDCl$_3$): δ 8.19-8.08 (m, 4H), 7.63-7.44 (m, 6H), 5.58 (dd, J=1.2, 3.6 Hz, 1H), 5.37 (dd, J=3.6, 10.4 Hz, 1H), 5.13 (d, J=3.7 Hz, 1H), 4.54-4.46 (m, 1H), 4.30-4.22 (m, 1H), 3.46 (s, 3H), 2.22 (d, J=6.1 Hz, 1H), 1.27 (d, J=6.6 Hz, 3H).

[(2S,3R,4R,5S)-5-benzoyloxy-4-(imidazole-1-carbothioyloxy)-6-methoxy-2-methyl-tetrahydropyran-3-yl] benzoate (235)

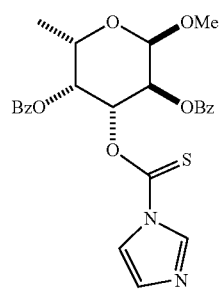

235

[(2S,3S,4R,5S)-5-benzoyloxy-4-hydroxy-6-methoxy-2-methyl-tetrahydropyran-3-yl] benzoate (234) (3.30 g, 8.54 mmol, 1.00 eq.) was dissolved in toluene (30 mL) and treated with 1,1-thiocarbonyldiimidazole (1826 mg, 10.2 mmol, 1.20 eq). The reaction was heated at 70° C. and monitored by LCMS. After 4 h, the reaction mixture was concentrated to give a crude product purified by flash chromatography, (40 g silica cartridge eluted with cyclohexane: ethyl acetate (1-35%)) to give the title compound (235) (4.08 g, 95%) as white solid. $^1$H NMR (300 MHz, CDCl$_3$): δ 8.13-8.09 (m, 3H), 8.02-7.98 (m, 2H), 7.69-7.62 (m, 1H), 7.60-7.49 (m, 3H), 7.46-7.39 (m, 2H), 7.36-7.34 (m, 1H), 6.86-6.84 (m, 1H), 6.41 (dd, J=3.3, 10.7 Hz, 1H), 5.90-5.88 (m, 1H), 5.79 (dd, J=3.8, 10.5 Hz, 1H), 5.23 (d, J=3.6 Hz, 1H), 4.45-4.38 (m, 1H), 3.52 (s, 3H), 1.32 (d, J=6.5 Hz, 3H).

Example 9: (2S,3S,5S,6R)-5-benzoyloxy-6-methoxy-2-methyl-tetrahydropyran-3-yl] benzoate (236)

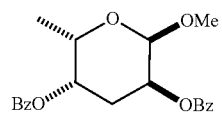

236

To a solution of [(2S,3R,4R,5S,6R)-5-benzoyloxy-4-(imidazole-1-carbothioyloxy)-6-methoxy-2-methyl-tetrahydropyran-3-yl] benzoate (235) (1.00 g, 2.01 mmol, 1.00 eq) in dry toluene (40 mL) at 55° C. was added 2,2-azobis(2-methylpropionitrile) (0.083 g, 0.503 mmol, 0.25 eq) and tributyltin hydride (1.1 mL, 4.03 mmol, 2.00 eq). The reaction mixture was heated at 90° C. for 24 h, concentrated and the residue purified by flash chromatography (24 g silica cartridge eluted with cyclohexane: ethyl acetate from 0 to 35%) to give the title compound (236) (567 mg, 72%) as a dense oil. $^1$H NMR (300 MHz, CDCl$_3$): δ 8.17-8.03 (m, 4H), 7.62-7.42 (m, 6H), 5.45-5.34 (m, 2H), 5.08 (d, J=3.4 Hz, 1H), 4.21 (dq, J=1.3, 6.6 Hz, 1H), 3.49 (s, 3H), 2.45 (ddd, J=12.9, 12.9, 3.0 Hz, 1H), 2.32-2.25 (m, 1H), 1.25 (d, J=6.6 Hz, 3H).

Scheme 7 illustrate preparation of compound 239.

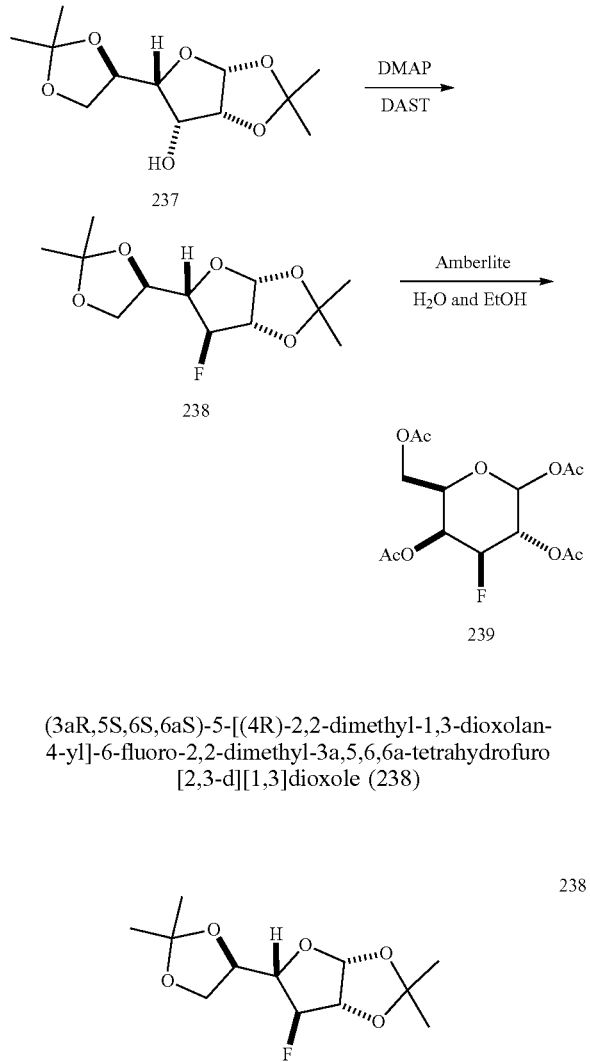

(3aR,5S,6S,6aS)-5-[(4R)-2,2-dimethyl-1,3-dioxolan-4-yl]-6-fluoro-2,2-dimethyl-3a,5,6,6a-tetrahydrofuro[2,3-d][1,3]dioxole (238)

1,2:5,6-Di-O-isopropylidene-α-D-gulofuranose (237) (3.00 g, 11.5 mmol, 1 eq.) was dissolved in dichloromethane (20 mL) and the solution cooled to −10° C. 4-(Dimethylamino)pyridine (2.82 g, 23.1 mmol, 2.00 eq) was added to the reaction mixture followed by slow addition of (Diethylamino)sulfur trifluoride (3.0 mL, 23.1 mmol, 2.00 eq). The reaction mixture was allowed to warm to room temperature and monitored by TLC (7:3 cyclohexane: ethyl acetate). After 24 h, a new spot at R$_f$ 0.7 was observed and the reaction mixture was cooled to −20° C., MeOH was slowly added while the temperature was maintained between −20° C. and −10° C. The mixture was allowed to warm to room temperature and then was partitioned between aqueous saturated NaHCO$_3$ and dichloromethane. The organic layer was passed through a phase separator cartridge and the solvent evaporated to give a crude product (4.1 g) purified by flash chromatography using cyclohexane: ethyl acetate (1 to 35%) to give the title compound (238) (3.0 g, 99%) as a colorless oil which later crystallized. $^1$H NMR (300 MHz, CDCl$_3$): d, 5.94 (d, J=3.8 Hz, 1H), 4.85 (dd, J=3.6, 40.8 Hz, 1H), 4.74 (dd, J=3.9, 3.9 Hz, 1H), 4.39-4.32 (m, 1H), 4.20-4.06 (m, 2H), 3.84 (dd, J=6.6, 8.3 Hz, 1H), 1.56 (s, 3H), 1.47 (s, 3H), 1.40 (s, 3H), 1.37 (s, 3H).

Example 10: [(2R,3S,4S,5S)-3,5,6-triacetoxy-4-fluoro-tetrahydropyran-2-yl]methyl acetate (239)

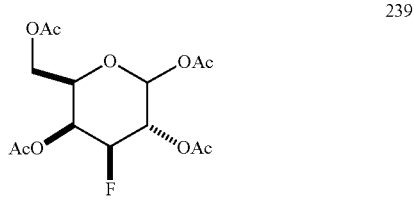 [SMILES: CC(=O)OC[C@H]1OC(OC(C)=O)[C@H](OC(C)=O)[C@@H](F)[C@H]1OC(C)=O]

3-Deoxy-3-fluoro-1,2:5,6-di-O-isopropylidene-α-D-galactofuranose (3aR,5S,6S,6aS)-5-[(4R)-2,2-dimethyl-1,3-dioxolan-4-yl]-6-fluoro-2,2-dimethyl-3a,5,6,6a-tetrahydrofuro[2,3-d][1,3]dioxole (238) (380 mg, 1.45 mmol, 1.00 eq) was dissolved in ethanol (16 mL) and water (33.00 mL). Amberlite IR-120 (H+) (ca. 3 mL) was added, and the reaction mixture was stirred at 60-65° C. and monitored by TLC (1:1 ethyl acetate: cyclohexane). After 4 h, TLC indicated the disappearance of starting material. The reaction mixture was filtered and concentrated in vacuo to give a crude product (216 mg) as the expected pyranose which was confirmed by $^1$H NMR. The crude material was dissolved in dry pyridine (3.00 mL), cooled to 0° C. under a nitrogen atmosphere and treated with acetic anhydride (0.68 mL, 7.24 mmol, 5.00 eq). The reaction mixture was allowed to warm to room temperature and monitored by TLC (3:7 ethyl acetate: cyclohexane). After 24 h, TLC showed a major sport at R$_f$ 0.5 for the expected product. The reaction mixture was concentrated, and the residue evaporated from toluene (5 mL). The crude oil was partitioned between ethyl acetate and aqueous saturated NaHCO$_3$. The organic layer was separated, dried (Na$_2$SO$_4$), filtered and the volatiles evaporated to give an oil (385 mg) which was purified by flash chromatography (12 g silica cartridge eluted with cyclohexane: ethyl acetate (2 to 50%)) gave the title compound (239) as an anomeric mixture (258 mg) of a colorless dense oil. $^1$H NMR (400 MHz, CDCl3): δ 6.42 (t, J=4.2, 1H), 5.72-5.68 (m, 1H), 5.67 (d, J=8.3 Hz, 1H), 5.62 (m, 1H), 5.48-5.39 (m, 2H), 4.97 (ddd, J=3.8, 10.2, 48.4 Hz, 1H), 4.71 (ddd, J=3.8, 9.7, 47.3 Hz, 1H), 4.33-4.29 (m, 1H), 4.25-4.07 (m, 4H), 4.00 (tt, J=1.5, 6.5 Hz, 1H), 2.21 (s, 3H), 2.20 (s, 3H), 2.18 (s, 3H), 2.16 (s, 3H), 2.13 (s, 3H), 2.10 (s, 3H), 2.09 (s, 3H), 2.08 (s, 3H).

Scheme 8 illustrate preparation of compound 242 and 243.

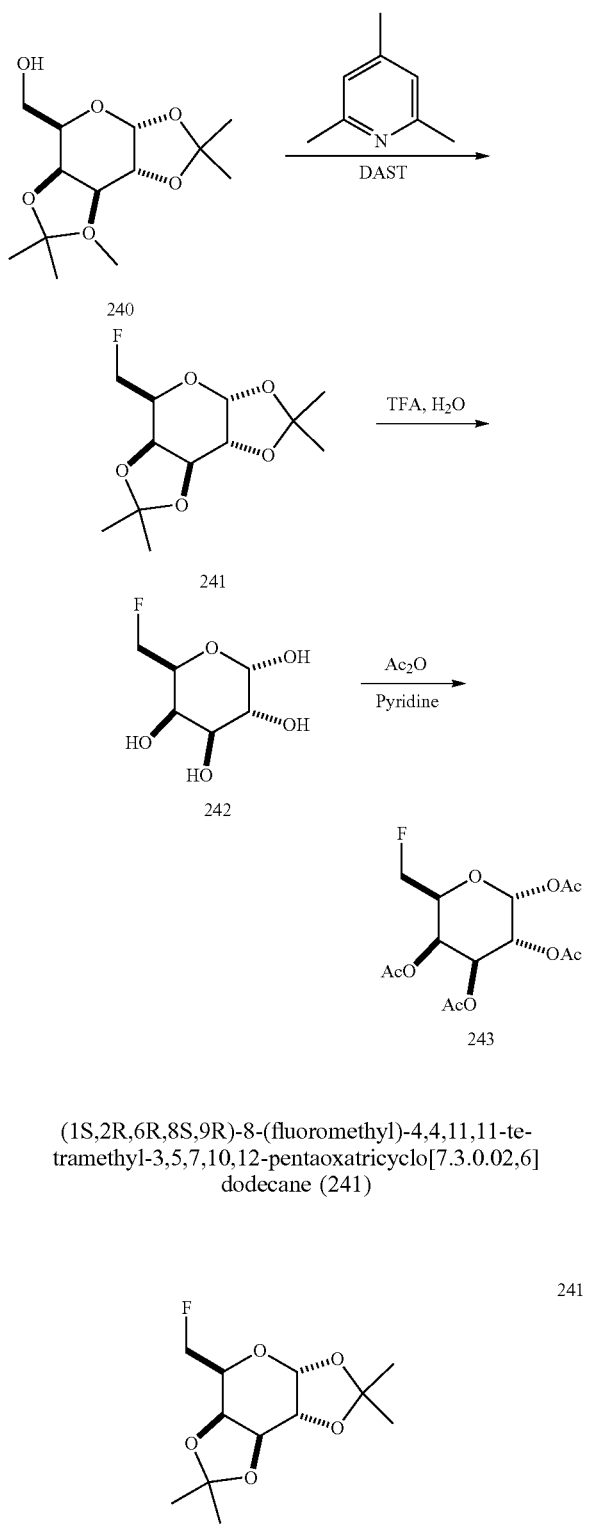

(1S,2R,6R,8S,9R)-8-(fluoromethyl)-4,4,11,11-tetramethyl-3,5,7,10,12-pentaoxatricyclo[7.3.0.02,6]dodecane (241)

To a solution of 1,2:3,4-Di-O-isopropylidene-alpha-D-galactopyranose (1.7 mL, 7.68 mmol, 1.00 eq) (240) in dichloromethane (20 mL) was added 2,4,6-trimethylpyridine (2.4 mL, 18.4 mmol, 2.40 eq). The mixture was cooled to 0° C. and treated with (diethylamino)sulfur trifluoride (1.2 mL, 9.22 mmol, 1.20 eq). The reaction mixture was allowed to stir at room temperature under nitrogen and monitored by TLC (ethyl acetate: cyclohexane 1:1). After 18 h the reaction mixture was diluted with dichloromethane, washed with aqueous saturated NaHCO₃, brine (25 mL), dried (Na₂SO₄) filtered and the volatiles evaporated. The residue was purified by silica flash chromatography eluting with ethyl acetate: cyclohexane (0-20%) to give the title compound (241) (913 mg, 45%) as a colorless syrup. ¹H NMR (300 MHz, CDCl₃): d, 5.55 (d, J=4.9 Hz, 1H), 4.69-4.58 (m, 2H), 4.48 (dq, J=6.1, 8.9 Hz, 1H), 4.35 (ddd, J=2.5, 2.5, 2.5 Hz, 1H), 4.27 (dd, J=2.0, 8.0 Hz, 1H), 4.13-4.03 (m, 1H), 1.55 (s, 3H), 1.45 (s, 3H), 1.34 (s, 6H).

Example 12: (3R,4S,5R,6S)-6-(fluoromethyl)tetrahydropyran-2,3,4,5-tetrol (242)

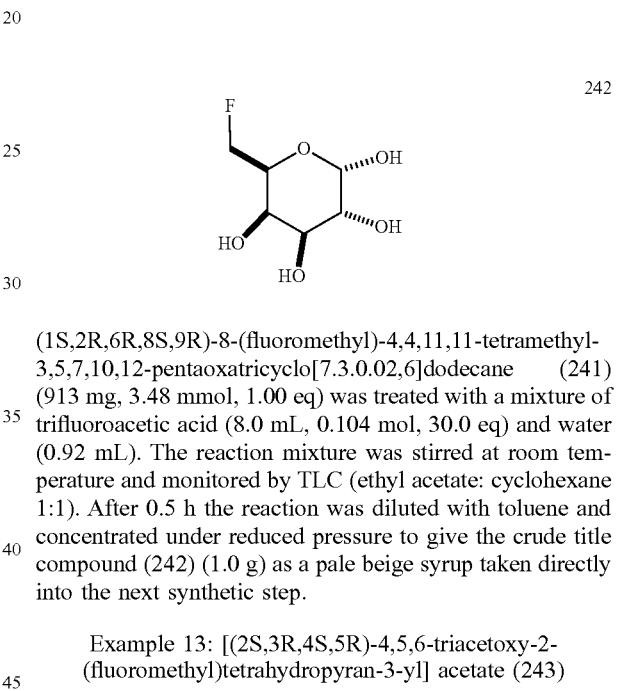

(1S,2R,6R,8S,9R)-8-(fluoromethyl)-4,4,11,11-tetramethyl-3,5,7,10,12-pentaoxatricyclo[7.3.0.02,6]dodecane (241) (913 mg, 3.48 mmol, 1.00 eq) was treated with a mixture of trifluoroacetic acid (8.0 mL, 0.104 mol, 30.0 eq) and water (0.92 mL). The reaction mixture was stirred at room temperature and monitored by TLC (ethyl acetate: cyclohexane 1:1). After 0.5 h the reaction was diluted with toluene and concentrated under reduced pressure to give the crude title compound (242) (1.0 g) as a pale beige syrup taken directly into the next synthetic step.

Example 13: [(2S,3R,4S,5R)-4,5,6-triacetoxy-2-(fluoromethyl)tetrahydropyran-3-yl] acetate (243)

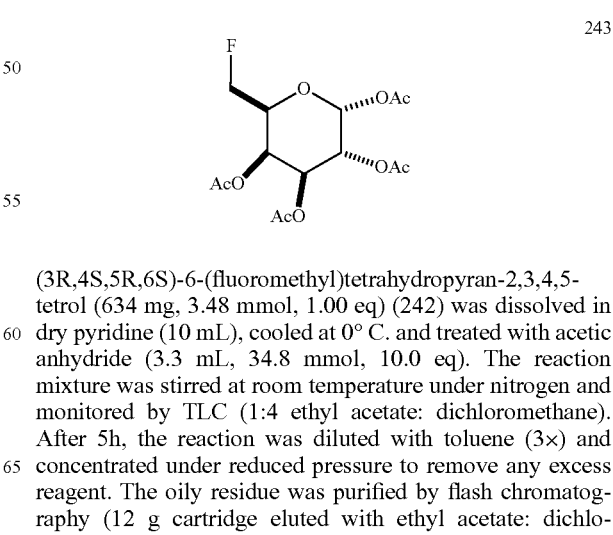

(3R,4S,5R,6S)-6-(fluoromethyl)tetrahydropyran-2,3,4,5-tetrol (634 mg, 3.48 mmol, 1.00 eq) (242) was dissolved in dry pyridine (10 mL), cooled at 0° C. and treated with acetic anhydride (3.3 mL, 34.8 mmol, 10.0 eq). The reaction mixture was stirred at room temperature under nitrogen and monitored by TLC (1:4 ethyl acetate: dichloromethane). After 5h, the reaction was diluted with toluene (3×) and concentrated under reduced pressure to remove any excess reagent. The oily residue was purified by flash chromatography (12 g cartridge eluted with ethyl acetate: dichloromethane (1:9)) to give the title compound (243) (960 mg, 79%) (anomeric mixture) as a colorless oil.

LCMS Methods:

Method A: Chromlith, C-18, 50×4.6 mm; 1.5 mL/minutes flow rate, ELSD and 254 nm UV detection; mobile phase A: 0.1% TFA in water; mobile phase B: 0.1% TFA in acetonitrile; 5 to 100% mobile phase B over 6 minutes; ambient temperature.

What is claimed is:

1. A compound Formula (II):

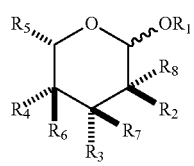

(II)

or pharmaceutically available salts, hydrate and solvates thereof, wherein:

$R_1$ is —$NH_2$;
$R_2$ is —H or —F;
$R_3$ is —H, —F, —OH, —OC(O)$R_{11}$ or —OC(O)O$R_{12}$;
$R_4$ is —H, —F, —OH, —OC(O)$R_{13}$ or —OC(O)O$R_{14}$;
alternatively, both $R_3$ and $R_4$ together with the atoms to which they are bonded form a 5 membered cyclic acetal which is substituted by $R_{19}$ at the acetal carbon;
alternatively, both $R_3$ and $R_4$ together with the atoms to which they are bonded form a 5 membered cyclic carbonate;
$R_5$ is —$CH_3$, —$CH_2OH$, —OC(O)$R_{17}$ or —OC(O)O$R_{18}$;
$R_6$ is —H or —F;
$R_7$ is —H or —F;
$R_8$ is —H or —F;
$R_9$-$R_{18}$ are independently alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloheteroalkyl, substituted cycloheteroalkyl, cycloheteroalkenyl, substituted cycloheteroalkenyl, heteroaryl or substituted heteroaryl; and
$R_{19}$ is alkyl, substituted alkyl, aryl, substituted aryl, cycloalkyl, substituted cycloalkyl, cycloheteroalkyl, substituted cycloheteroalkyl, heteroaryl or substituted heteroaryl.

2. The compound of claim 1, wherein $R_9$-$R_{19}$ are independently alkyl, alkenyl, aryl, substituted aryl, cycloalkyl or cycloheteroalkyl.

3. The compound of claim 1, wherein $R_9$-$R_{19}$ are independently ($C_1$-$C_4$) alkyl, ($C_1$-$C_4$) alkenyl, phenyl, substituted phenyl, ($C_5$-$C_7$) cycloalkyl or ($C_5$-$C_7$) cycloheteroalkyl.

4. The compound of claim 1, wherein $R_9$-$R_{19}$ are independently ($C_1$-$C_4$) alkyl, ($C_1$-$C_4$) alkenyl, phenyl or substituted phenyl.

5. The compound of claim 1, wherein $R_9$-$R_{19}$ are independently ($C_1$-$C_4$) alkyl, ($C_1$-$C_4$) alkenyl, phenyl, substituted phenyl, benzyl or substituted benzyl.

6. A compound having the structure:

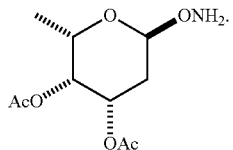

* * * * *

UNITED STATES PATENT AND TRADEMARK OFFICE
CERTIFICATE OF CORRECTION

PATENT NO. : 11,897,915 B2  
APPLICATION NO. : 17/944019  
DATED : February 13, 2024  
INVENTOR(S) : Paul Keitz et al.

Page 1 of 1

It is certified that error appears in the above-identified patent and that said Letters Patent is hereby corrected as shown below:

In the Claims

Claim 1, Line 1, "$R_9$-$R_{18}$" should read -$R_{11}$-$R_{18}$-.  
Claim 2, Line 12, "$R_9$-$R_{18}$" should read -$R_{11}$-$R_{18}$-.  
Claim 3, Line 16, "$R_9$-$R_{18}$" should read -$R_{11}$-$R_{18}$-.  
Claim 4, Line 20 "$R_9$-$R_{18}$" should read -$R_{11}$-$R_{18}$-.  
Claim 5, Line 23, "$R_9$-$R_{18}$" should read -$R_{11}$-$R_{18}$-.

Signed and Sealed this  
Fifteenth Day of October, 2024

Katherine Kelly Vidal  
*Director of the United States Patent and Trademark Office*